US012329572B2

(12) United States Patent
Giphart et al.

(10) Patent No.: US 12,329,572 B2
(45) Date of Patent: Jun. 17, 2025

(54) COMPOSITE ULTRASOUND IMAGES

(71) Applicant: ArcScan, Inc., Golden, CO (US)

(72) Inventors: Johan E. Giphart, Aurora, CO (US); Matthew G. Sassu, Denver, CO (US); Andrew K. Levien, Morrison, CO (US); John D. Watson, Evergreen, CO (US)

(73) Assignee: ArcScan, Inc., Golden, CO (US)

( * ) Notice: Subject to any disclaimer, the term of this patent is extended or adjusted under 35 U.S.C. 154(b) by 0 days.

(21) Appl. No.: 18/537,379

(22) Filed: Dec. 12, 2023

(65) Prior Publication Data

US 2024/0180517 A1 Jun. 6, 2024

Related U.S. Application Data

(62) Division of application No. 17/143,705, filed on Jan. 7, 2021, now Pat. No. 11,839,510.

(60) Provisional application No. 62/970,099, filed on Feb. 4, 2020, provisional application No. 62/963,445, filed on Jan. 20, 2020, provisional application No. 62/958,111, filed on Jan. 7, 2020.

(51) Int. Cl.
*A61B 8/10* (2006.01)
*A61B 8/00* (2006.01)

(52) U.S. Cl.
CPC ............. *A61B 8/10* (2013.01); *A61B 8/5246* (2013.01)

(58) Field of Classification Search
CPC .. A61B 3/113; A61B 8/10; A61B 8/40; A61B 8/4416; A61B 8/5246; A61B 8/5261
See application file for complete search history.

(56) References Cited

U.S. PATENT DOCUMENTS

2013/0144171 A1* 6/2013 Watson ................ A61B 8/0858
600/452

* cited by examiner

Primary Examiner — Mark D Remaly
(74) Attorney, Agent, or Firm — Sheridan Ross P.C.

(57) ABSTRACT

Systems, processes, and apparatuses are provided for imaging a body part of a patient such as an eye of the patient. In some embodiments, a process is provided for adjusting the readings from an ultrasound probe to account for the different speeds of sound through different portions of the eye. In various embodiments, a process is provided for combing multiple images of the body part together. In some embodiments, a process is provided for determining the diameter of the lens of the eye.

20 Claims, 27 Drawing Sheets

COMPOSITE ULTRASOUND IMAGES

CROSS-REFERENCE TO RELATED APPLICATIONS

This application is a division of U.S. patent application Ser. No. 17/143,705, entitled "Composite Ultrasound Images", filed on Jan. 7, 2021, now U.S. Pat. No. 11,839,510, issued on Dec. 12, 2023, which claims the benefits, under 35 U.S.C. § 119(e), of U.S. Provisional Application Ser. No. 62/958,111 entitled "Ultrasound Images", filed Jan. 7, 2020; of U.S. Provisional Application Ser. No. 62/963,445 entitled "Ultrasound Images", filed Jan. 20, 2020; and of U.S. Provisional Application Ser. No. 62/970,099 entitled "Ultrasound Images", filed Feb. 4, 2020, all of which are incorporated herein by reference in their entireties.

FIELD OF INVENTION

The present disclosure describes a method for adjusting ultrasound images for eye movement during scanning; for instrument movement during scanning; for variations in the speed of sound through different regions within the eye; or for transducer path optimization using scout images.

BACKGROUND OF THE INVENTION

Ultrasound

Ultrasonic imaging has found use in accurate and reproducible measurements of structures of the eye, such as, for example, the cornea and lens capsule. Such measurements provide an ophthalmic surgeon valuable information that can be used to guide various surgical procedures for correcting refractive errors such as LASIK and lens replacement. They also provide diagnostic information after surgery has been performed to assess the geometrical location of corneal features such as the LASIK scar and lens features such as lens connection, position and orientation. This allows the surgeon to assess post surgical changes in the cornea or lens and to take steps to correct any problems that develop.

Except for on-axis measurements, dimensions and locations of eye components behind the iris cannot be fully determined by optical means. Ultrasonic imaging in the frequency range of about 5 MHz to about 80 MHz can be applied to make accurate and precise measurements of structures of the eye, such as the cornea, lens capsule, ciliary muscle and the like.

An ultrasound scanning apparatus is described in the following issued US patents, all of which are incorporated herein by reference:
1. U.S. Pat. No. 7,048,690 "Precision Ultrasound Measurement for Intraocular Lens Placement";
2. U.S. Pat. No. 8,758,252 "Innovative Components for an Ultrasonic Arc Scanning Apparatus";
3. U.S. Pat. No. 8,496,588 "Procedures for an Ultrasonic Arc Scanning Apparatus"
4. U.S. Pat. No. 8,317,709 "Alignment and Imaging of an Eye with an Ultrasonic Scanner"
5. U.S. Pat. No. 9,149,254 "Alignment and Imaging of an Eye with an Ultrasonic Scanner"
6. U.S. Pat. No. 9,597,059 "Tracking Unintended Eye Movements in an Ultrasonic Scan of the Eye"

At a center frequency of about 38 MHz, a typical arc scanner has an axial resolution of about 20 microns and a lateral resolution of about 150 microns. The reproducibility of arc scanner images is typically about 2 microns.

The ultrasonic system described herein is capable of accurately moving an ultrasound transducer with respect to a known reference point on a patient's head. Further improvements allow for tracking of unintended eye motions during scanning as disclosed in U.S. Pat. No. 9,597,059 entitled "Tracking Unintended Eye Movements in an Ultrasonic Scan of the Eye" which is incorporated herein by reference.

Ultrasonic imaging has been used in corneal procedures such as LASIK to make accurate and precise images and maps of cornea thickness which include epithelial thickness, Bowman's layer thickness and images of LASIK flaps. At a center frequency of about 38 MHz, a typical arc scanner image has an axial resolution of about 20 microns and a lateral resolution of about 150 microns. The operator and instrument reproducibility of an arc scanner image is typically about 2 microns.

New procedures such as implantation of accommodative lenses may provide nearly perfect vision without spectacles or contact lenses. Implantation of accommodative lenses requires precision measurements of, for example, the position and width of the natural lens for successful lens powering and implantation. Ultrasonic imaging can be used to provide the required accurate images of the natural lens especially where the zonules attach the lens to the ciliary body which is well off-axis and behind the iris and therefore not accessible to optical imaging.

Recent advances in ultrasonic imaging have allowed images of substantially the entire lens capsule to be made. This has opened up the ability of diagnostic devices to assist in both research of lens implantation devices and strategies, and to planning, executing and follow-up diagnostics for corrective lens surgery including specialty procedures such as glaucoma and cataract treatments as well as implantation of clear intraocular lenses including accommodative lens.

A phakic intraocular lens (PIOL) is a special kind of intraocular lens that is implanted surgically into the eye to correct myopia. It is called "phakic" (meaning "having a lens") because the eye's natural lens is left untouched. Intraocular lenses that are implanted into eyes after the eye's natural lens has been removed during cataract surgery are known as pseudophakic. Phakic intraocular lenses are considered for patients with high refractive errors when laser options, such as LASIK and PRK are not the best surgical options.

Ultrasound provides key measurements behind iris not before available and can reduce explant rates by about ten times.

Other new procedures such as implantation of stents in or near the suprachoroid may provide part or all of a treatment for glaucoma. Ultrasonic imaging can be used to provide the required accurate images in the corner of the eye between the sclera and the iris (in the region of the suprachoroidal space to the scleral spur) which is well off-axis and essentially inaccessible to optical imaging.

An ultrasonic scan of the eye may include one or more B-scans (each B-scan formed from a plurality of A-scans) and these may be combined automatically to form a comprehensive image of the anterior segment. Therefore it is necessary to rapidly scan a patient to reduce the possibility of patient eye motion during a scan session. Rapid scans can cause motion of the instrument as the transducer carriage and scan head move back and forth in the water bath.

Both ultrasound sector and ultrasound arc scanning instruments record time-of-arrival of reflected ultrasound pulses. A speed of sound of the medium is then used to convert these time of arrival measurements to distance measurements.

Traditionally, a single representative speed of sound value is used. Usually the speed of sound of water at 37C (1,531 m/s) is used although speeds of sound from 1,531 m/s to 1,641 m/s may be used (1,641 m/s is the speed of sound in a natural human lens).

The speed of sound varies in the different anterior segment regions of the eye such as the cornea, aqueous, natural lens and vitreous fluid. The speed of sound in these different regions have been measured by various researchers and are reasonably known. Therefore if the interfaces of these regions can be identified, the appropriate speeds of sounds for these regions can be used to convert times of arrivals to distances with more accuracy.

It is also important to compensate for unintended patient head or eye motion because a scan of the anterior segment scan or lens capsule scan is typically made by overlaying two or three separate scans (such as an arcuate scan followed by two linear scans, also described in U.S. Pat. No. 9,597,059 entitled "Tracking Unintended Eye Movements in an Ultrasonic Scan of the Eye".

Unintended patient eye motion includes saccades which are quick, simultaneous rotations of both eyes in the same direction involving a succession of discontinuous individual rotations of the eye orbit in the eye socket.

The speed of transducer motion in a precision scanning device such as described, for example, in U.S. Pat. No. 8,317,709, is limited because its movement is in a bath of water and excessive speed of motion of the transducer and its carriage can result in vibration of the entire instrument. In practice, a set of ultrasound scans can be carried out in about 1 to about 3 minutes from the time the patient's eye is immersed in water to the time the water is drained from the eyepiece.

The actual scanning process itself can be carried out in several tens of seconds, after the operator or automated software completes the process of centering and range finding. As is often the case, the patient may move his or her head slightly or may move his or her eye in its socket during this time. In some cases, the patient's heart beat can be detected as a slight blurring of the images. If patient movements are large, the scan set can always be repeated.

The arc scanning instrument of the present disclosure can create several distinct scan types. These are:
  $ an arcuate scan having a fixed radius of curvature
  $ a linear scan
  $ a combined arcuate and linear scan allowing for various radii of curvature including inverse radii of curvature These scans can be combined to form composite images because each image is formed from very accurate time-of-arrival data and transducer positional data. However, combining these separate scans into a composite scan must take into account patient eye movement during scanning; and instrument movement during scanning.

Due to the need for an eye seal to provide a continuous medium for the ultrasound signal to travel between the transducer, any scanning device has a limitation in the range of movement the transducer can make relative to the eye. The range of the scanning device can be expanded to cover more of the anterior segment by introducing intentional and controlled eye movements and scanning the newly exposed portion of the eye that can now be reached. Registration techniques can be used to combine the scans of different eye positions to create a more complete composite image of the anterior segment of the eye.

U.S. patent application Ser. No. 16/422,182 entitled "Method for Measuring Behind the Iris after Locating the Scleral Spur" is pending. This application is directed towards a method for locating the scleral spur in an eye using a precision ultrasound scanning device for imaging of the anterior segment of the eye. One of the applications of a precision ultrasound scanning device or instrument is to image the region of the eye where the cornea, iris, sclera and ciliary muscle are all in close proximity. By using a knowledge of the structure of the eye in this region and employing binary filtering techniques, the position of the scleral spur can be determined. Once the position of the scleral spur is determined, a number of measurements that characterize the normal and abnormal shapes of components within this region of the anterior segment of the eye can be made. Many of the ideas disclosed in this application may be used to form accurate composite images.

There remains, therefore, a need for a method for adjusting ultrasound images for eye movement during scanning; for instrument movement during scanning; and for variations in the speed of sound through different regions within the eye.

SUMMARY OF THE INVENTION

These and other needs are addressed by the present disclosure. The various embodiments and configurations of the present disclosure are directed generally to ultrasonic imaging of biological materials such as the cornea, sclera, iris and lens in the anterior segment of an eye and in particular directed to a method for adjusting ultrasound images for eye movement during scanning; for instrument movement during scanning; for variations in the speed of sound through different regions within the eye; or for transducer path optimization using scout images.
Adjustments for Speed of Sound Variation

Method 1

In a first method, an array of A-scans in volts versus time format is transformed into volts versus distance format by dividing by an appropriate average speed of sound. The positions of the prominent specular surfaces are identified and then the known speeds of sound for the regions between the specular surfaces are applied to adjust the positions of the specular surfaces. The array of A-scans in volts versus time format is re-transformed into volts versus distance format by dividing by the appropriate speed of sound for each region between specular surfaces.

Method 2

In a second method, an anatomical model with appropriate speed of sound for each region between specular surfaces can be deformed by computer algorithm to match a particular B-scan of an eye of interest using image or edge-based registration. This, in turn, allows a computer algorithm to re-apply the appropriate speed of sound to each anatomical region of the A-scan as described above for the first method.
Adjustments for Patient Eye Motion and Instrument Vibration During scanning, a patient's eye can move or the scanner can vibrate under the motion of the transducer. The movement of the transducer during a scan can be slowed to avoid instrument vibration but it is desirable to move the transducer probe as rapidly as possible to reduce scan time. A composite B-scan can comprise several intermediate B-scans and, when combined to form a composite image, may not align perfectly. The individual B-scans can be better aligned by overlaying one of the specular surfaces common to each B-scan to bring the separate images into alignment.

Compositing Images

The perpendicularity ultrasound beam requirement for optimal ultrasound imaging means that different anatomical structures may be imaged optimally by different transducer probe sweeps or trajectories. To create a complete picture of the anatomy of the eye, registering and merging different B-scan images, each formed from different sweeps enables the display of anatomically correct combinations of these images. Initial registration from instrument position data is critical for rapid convergence of high precision registration. To create a complete picture of the anatomy of the eye, registering and merging images from different sweeps enables the display of anatomically correct combinations of these images. The individual B-scans can be aligned by overlaying one of the specular surfaces common to each B-scan to bring the separate images into alignment.

Optimal Transducer Trajectory

A scout image or scout view is used, for example, to image locations where more features of interest may be obtained. An ultrasound scout image can be made from any of the scan types described above but is more commonly generated by the simpler scan types such as a cornea scan, an anterior segment scan, a central posterior capsule scan or a left and right segment scan of the posterior capsule. A scout image is used to identify the location of anatomy of interest and then to determine the trajectory of the transducer to optimally image that anatomy by maximizing perpendicularity while maintaining the anatomy at the focal length of the transducer during the one or more imaging sweep(s).

Estimating Lens Diameter

Imaging

A method of imaging the equatorial diameter of a lens is disclosed wherein the eye is dilated, then the eye is rotated and a number of small constant positive radius of curvature scans is prescribed. These images are stitched together to form a composite image of the natural lens from which the equatorial diameter of the lens can be estimated to within a few tens of microns.

Estimating from a Prior Data Base

A method of estimating the equatorial diameter of a lens without resorting to phakometry or magnetic resonance imaging wherein is disclosed wherein previously published biometry and phakometry data is used to define multiple linear regressions for the radii of curvature and thickness of the lens, from which the lens refractive index could be derived. MRI biometry can be used to determine for the vertex radii of curvature, conic constants, equatorial diameter, volume, and surface area.

The preceding is a simplified summary of the invention to provide an understanding of some aspects of the invention. This summary is neither an extensive nor exhaustive overview of the invention and its various embodiments. It is intended neither to identify key or critical elements of the invention nor to delineate the scope of the invention but to present selected concepts of the invention in a simplified form as an introduction to the more detailed description presented below. As will be appreciated, other embodiments of the invention are possible utilizing, alone or in combination, one or more of the features set forth above or described in detail below.

The following definitions are used herein:

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The phrases at least one, one or more, and or are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

An acoustically reflective surface or interface is a surface or interface that has sufficient acoustic impedance difference across the interface to cause a measurable reflected acoustic signal. A specular surface is typically a very strong acoustically reflective surface.

Anterior means situated at the front part of a structure; anterior is the opposite of posterior.

An A-scan is a representation of a rectified, filtered reflected acoustic signal as a function of time, received by an ultrasonic transducer from acoustic pulses originally emitted by the ultrasonic transducer from a known fixed position relative to an eye component.

An accommodative lens, also known as a presbyopic lens or presby lens, is an artificial intraocular lens that changes its focal distance in response to contraction of the ciliary body. When successfully implanted, an accommodative lens reverses presbyopia, the inability of the eye to change its focal distance from far to near.

Accuracy as used herein means substantially free from measurement error.

Aligning means positioning the acoustic transducer accurately and reproducibly in all three dimensions of space with respect to a feature of the eye component of interest (such as the center of the pupil, center of curvature or boundary of the cornea, lens, retina, etcetera).

The anterior chamber comprises the region of the eye from the cornea to the iris.

The anterior chamber depth ("ACD") is minimum distance from the posterior cornea surface to the anterior lens surface.

The anterior segment comprises the region of the eye from the front of the cornea to the back of the lens.

Automatic refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Auto-centering means automatically, typically under computer control, causing centration of the arc scanning transducer with the eye component of interest.

A B-scan is a processed representation of A-scan data by either or both of converting it from a time to a distance using acoustic velocities and by using grayscales, which correspond to A-scan amplitudes, to highlight the features along the A-scan time history trace (the latter also referred to as an A-scan vector).

Center of rotation of the eye, there is a point within the eyeball that is more or less fixed relative to the orbit when the eye rotates in its orbit. It is considered that the center of rotation of an emmetropic eye (that is, a normal eye with about 20/20 vision) lies on the line of sight of the eye about 13.5 mm behind the anterior pole of the cornea when the line of sight of the eye is perpendicular to both the base line and the frontal plane.

The ciliary body is the circumferential tissue inside the eye composed of the ciliary muscle and ciliary processes. There are three sets of ciliary muscles in the eye, the longitudinal, radial, and circular muscles. They are near the front of the eye, above and below the lens. They are attached to the lens by connective tissue called the zonule of Zinn, and are responsible for shaping the lens to focus light on the retina. When the ciliary muscle relaxes, it flattens the lens, generally improving the focus for farther objects. When it contracts, the lens becomes more convex, generally improving the focus for closer objects.

A composite image is an image that is made from the combination of multiple images merged onto a common co-ordinate system.

Compositing is the combining of images or image elements from separate sources into a single image. As used herein, compositing is achieved through digital image manipulation.

The term computer-readable medium as used herein refers to any tangible storage and/or transmission medium that participate in providing instructions to a processor for execution. Such a medium may take many forms, including but not limited to, non-volatile media, volatile media, and transmission media. Non-volatile media includes, for example, NVRAM, or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a CD-ROM, any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the invention is considered to include a tangible storage medium or distribution medium and prior art-recognized equivalents and successor media, in which the software implementations of the present invention are stored.

The terms determine, calculate and compute, and variations thereof, as used herein, are used interchangeably and include any type of methodology, process, mathematical operation or technique.

Fiducial means a reference, marker or datum in the field of view of an imaging device.

Fixation means having the patient focus an eye on an optical target such that the eye's optical axis is in a known spatial relationship with the optical target. In fixation, the light source is axially aligned in the arc plane with the light source in the center of the arc so as to obtain maximum signal strength such that moving away from the center of the arc in either direction results in signal strength diminishing equally in either direction away from the center.

The home position of the imaging ultrasound transducer is its position during the registration process.

Image stitching is the process of combining multiple B-scan images with overlapping fields of view to produce a composite B-scan.

An imaging ultrasound transducer is the device that is responsible for creating the outgoing ultrasound pulse and detecting the reflected ultrasound signal that is used for creating the A-Scans and B-Scans.

An intraocular lens is an artificial lens that is implanted in the eye to take the place of the natural lens.

LASIK is a procedure performed on the cornea for correcting refractive errors, such as myopia, hyperopia, and astigmatism. Commonly, an excimer laser selectively removes tissue from the inside of the cornea, after it is exposed, by cutting a thin flap, so as to reshape the external shape of the cornea.

The term module as used herein refers to any known or later developed hardware, software, firmware, artificial intelligence, fuzzy logic, or combination of hardware and software that is capable of performing the functionality associated with that element. Also, while the invention is described in terms of exemplary embodiments, it should be appreciated that individual aspects of the invention can be separately claimed.

The natural lens (also known as the aquula or crystalline lens) is a transparent, biconvex structure in the eye that, along with the cornea, helps to refract light to be focused on the retina. The lens, by changing shape, functions to change the focal distance of the eye so that it can focus on objects at various distances, thus allowing a sharp real image of the object of interest to be formed on the retina. This adjustment of the lens is known as accommodation. The lens is located in the anterior segment of the eye behind the iris. The lens is suspended in place by the zonular fibers, which attach to the lens near its equatorial line and connect the lens to the ciliary body. The lens has an ellipsoid, biconvex shape whose size and shape can change due to accommodation and due to growth during aging. The lens is comprised of three main parts: namely the lens capsule, the lens epithelium, and the lens fibers. The lens capsule forms the outermost layer of the lens and the lens fibers form the bulk of the interior of the lens. The cells of the lens epithelium, located between the lens capsule and the outermost layer of lens fibers, are generally found only on the anterior side of the lens.

Ophthalmology means the branch of medicine that deals with the eye.

Optical as used herein refers to processes that use light rays.

The optical axis of the eye is a straight line through the centers of curvature of the refracting surfaces of an eye (the anterior and posterior surfaces of the cornea and lens).

Phakic intraocular lenses, or phakic lenses, are lenses made of plastic or silicone that are implanted into the eye permanently to reduce a person's need for glasses or contact lenses. Phakic refers to the fact that the lens is implanted into the eye without removing the eye's natural lens. During phakic lens implantation surgery, a small incision is normally made in the front of the eye. The phakic lens is inserted through the incision and placed just in front of or just behind the iris.

Positioner means the mechanism that positions a scan head relative to a selected part of an eye. In the present disclosure, the positioner can move back and forth along the x, y or z axes and rotate in the $\beta$ direction about the z-axis. Normally the positioner does not move during a scan, only the scan head moves. In certain operations, such as measuring the thickness of a region, the positioner may move during a scan.

Position tracking sensors are a set of position sensors whose sole purpose is to monitor the movement of the eye or any other anatomical feature during the imaging scan so as to remove unwanted movement of the feature.

Posterior means situated at the back part of a structure; posterior is the opposite of anterior.

The posterior chamber comprises the region of the eye from the back of the iris to the front of the lens.

The posterior segment comprises the region of the eye from the back of the lens to the rear of the eye comprising the retina and optical nerve.

Precise as used herein means sharply defined and repeatable.

Precision means how close in value successive measurements fall when attempting to repeat the same measurement between two detectable features in the image field. In a normal distribution precision is characterized by the standard deviation of the set of repeated measurements. Precision is very similar to the definition of repeatability.

The pulse transit time across a region of the eye is the time it takes a sound pulse to traverse the region.

Registration as used herein means aligning.

Saccades are quick, simultaneous rotations of both eyes in the same direction involving a succession of discontinuous individual rotations of the eye orbit in the eye socket. These rapid motions can be on the order of 20 degrees of rotation with a maximum velocity of 200 degrees/sec and are a part of normal eyesight.

Scan head means the mechanism that comprises the ultrasound transducer, the transducer holder and carriage as well as any guide tracks that allow the transducer to be moved relative to the positioner. Guide tracks may be linear, arcuate or any other appropriate geometry. The guide tracks may be rigid or flexible. Normally, only the scan head is moved during a scan.

A scout image is an image taken in order to find the anatomy of interest in preparation for a useable image showing the anatomy of interest. The scout image may be used or deleted as appropriate. A scout image or scout view is a preliminary image obtained prior to performing the major portion of a particular study and is used, for example, to plot the locations where the subsequent slice images will be obtained. Many radiologists consider CT scout images to be merely a guide for correlating the levels of axial images. Unfortunately, in many instances, those scout images show critical diagnostic information that is not displayed on the axial images, particularly in cranial, thoracic, and abdominal studies.

A scout film is a preliminary film taken of a body region before a definitive imaging study—e.g., a scout film of the chest before a CT. "Scouts" serve to establish a baseline and may be used before performing angiography, CT, or MRI.

Sector scanner is an ultrasonic scanner that sweeps a sector like a radar. The swept area is pie-shaped with its central point typically located near the face of the ultrasound transducer.

A specular surface means a mirror-like surface that reflects either optical or acoustic waves. For example, an ultrasound beam emanating from a transducer will be reflected directly back to that transducer when the beam is aligned perpendicular to a specular surface.

A track or guide track is an apparatus along which another apparatus moves. In an ultrasound scanner or combined ultrasound and optical scanner, a guide track is an apparatus along which one or more ultrasound transducers and/or optical probes moves during a scan.

Ultrasonic means sound that is above the human ear's upper frequency limit. When used for imaging an object like the eye, the sound passes through a liquid medium, and its frequency is many orders of magnitude greater than can be detected by the human ear. For high-resolution acoustic imaging in the eye, the frequency is typically in the approximate range of about 5 to about 80 MHz.

An ultrasonic scanner is an ultrasound scanning device utilizing a transducer that both sends and receives pulses as it moves along 1) an arcuate guide track, which guide track has a center of curvature whose position can be moved to scan different curved surfaces; 2) a linear guide track; and 3) a combination of linear and arcuate guide tracks which can create a range of centers of curvature whose position can be moved to scan different curved surfaces.

A vector refers to a single acoustic pulse and its multiple reflections from various eye components. An A-scan is a representation of this data whose amplitude is typically rectified.

One specific embodiment of the present disclosure is a process for adjusting data from an A-Scan, comprising providing signal-versus-time data from an A-Scan; converting the signal-versus-time data to distance-versus-time data by dividing the signal-versus-time data by an average sound speed; identifying a specular surface in the distance-versus-time data, wherein the specular surface divides a first non-specular region from a second non-specular region, and a first sound speed is associated with the first non-specular region and a second sound speed is associated with the second non-specular region, wherein the first sound speed and the second sound speed are distinct; and converting the signal-versus-time data to adjusted distance-versus-time data by dividing the signal-versus-time data by the first sound speed in the first non-specular region and by the second sound speed in the second non-specular region.

In some embodiments, the process further comprises determining the signal-versus-time data by applying a Fourier transform to initial signal-versus-time data, removing negative frequencies, and then applying an inverse Fourier transform. In various embodiments, the process further comprises determining a time-to-arrival value for the specular surface from the distance-versus-time data, and wherein the first non-specular region extends between a first time value and the time-to-arrival value, and the second non-specular region extends between the time-to-arrival value and a second time value. In some embodiments, the average sound speed is approximately 1531 m/s, the first sound speed is approximately 1639 m/s, and the second sound speed is approximately 1532 m/s such that the first non-specular region is within a cornea of an eye, and the second non-specular region is within an aqueous portion of the eye. In various embodiments, the average sound speed is equal to one of the first sound speed or the second sound speed.

In some embodiments, the process further comprises applying a grayscale color scheme to the adjusted distance-versus-time data where black from the grayscale color scheme corresponds to a signal of zero and a stronger intensity from the grayscale color scheme corresponds to a larger signal; and plotting intensity-versus-distance data from the grayscale color scheme and the adjusted distance-versus-time data to produce an adjusted B-Scan. In various embodiments, identifying the specular surface comprises identifying a local maximum of the distance-versus-time data or, alternately, matching an anatomical model on the B-scan to assist with identifying the speed of sound regions.

Another particular embodiment of the present disclosure is a process for combining multiple images of a body part, comprising providing a first grayscale image of a body part and a second grayscale image of the body part; overlaying the first and second images and moving the first and second images relative to each other; determining an alignment parameter at each relative position between the first and second images until the alignment parameter is at an extremum at one relative position; and combining the first and second images on a pixel-by-pixel basis at the one relative position with the extremum, wherein if an aligned pixel has a value above a predetermined threshold in both images, then intensities of the pixels from both images are averaged together in the combined image, and wherein if an aligned pixel has a value above a predetermined threshold in only one image, then an intensity of the pixel above the predetermined threshold is used in the combined image.

In some embodiments, determining the alignment parameter is a sum of squared residuals from each pixel, and the extremum is a minimum value of the sum. In various embodiments, the predetermined threshold is an intensity value from a grayscale color scheme. In some embodiments, the process further comprises translating and rotating the first and second images relative to each other to move the first and second images relative to each other.

In various embodiments, the process further comprises only translating the first and second images relative to each other to move the first and second images relative to each other. In some embodiments, the first image is produced from ultrasound signals from an ultrasound probe moving in a first sweep pattern, and the second image is produced from ultrasound signals from an ultrasound probe moving in a distinct, second sweep pattern. In various embodiments, the first image begins at the anterior surface of a cornea and the second image ends at the posterior surface of a lens.

Yet another particular embodiment of the present disclosure is a process for determining a lens diameter of an eye, comprising providing an ultrasound probe operably connected to an arcuate track and a linear track; scanning the eye of the patient with the ultrasound probe in a first sweep pattern after the eye of the patient rotates to one side; generating a B-Scan from the signals received by the ultrasound probe moving in the first sweep pattern, wherein at least one anatomical surface of the eye of the patient is identified; scanning the at least one anatomical surface of the eye of the patient with the ultrasound probe in a second sweep pattern after the eye of the patient rotates to the one side, wherein the second sweep pattern is distinct from the first sweep pattern; and generating another B-Scan from the signals received by the ultrasound probe moving in the second sweep pattern.

In some embodiments, the first sweep pattern is a radius of curvature between approximately 7 to 11 mm, and the second sweep pattern includes a radius of curvature of approximately 4 mm. In various embodiments, at least one of the first sweep pattern and the second sweep pattern combines linear motion from the linear track and arcuate motion from the arcuate track. In some embodiments, the process further comprises combining the B-Scan associated with the second sweep pattern with at least one other B-Scan to produce a composite image of a lens of the eye. In various embodiments, the process further comprises determining an equatorial diameter of the lens of the eye from radii of curvature of an anterior and a posterior of a cornea of the eye and from radii of curvature of an anterior and a posterior of the lens. In some embodiments, the process further comprises adjusting the A-Scans that form the B-Scan associated with the first sweep pattern by dividing signal-versus-time data by a first sound speed in a first non-specular region and by a distinct, second sound speed in a second non-specular region.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein. By way of example, the phrase from about 2 to about 4 includes the whole number and/or integer ranges from about 2 to about 3, from about 3 to about 4 and each possible range based on real (e.g., irrational and/or rational) numbers, such as from about 2.1 to about 4.9, from about 2.1 to about 3.4, and so on.

The preceding is a simplified summary of the disclosure to provide an understanding of some aspects of the disclosure. This summary is neither an extensive nor exhaustive overview of the disclosure and its various embodiments. It is intended neither to identify key or critical elements of the disclosure nor to delineate the scope of the disclosure but to present selected concepts of the disclosure in a simplified form as an introduction to the more detailed description presented below. As will be appreciated, other embodiments of the disclosure are possible utilizing, alone or in combination, one or more of the features set forth above or described in detail below.

BRIEF DESCRIPTION OF THE DRAWINGS

The present disclosure may take form in various components and arrangements of components, and in various steps and arrangements of steps. The drawings are only for purposes of illustrating the preferred embodiments and are not to be construed as limiting the invention. In the drawings, like reference numerals may refer to like or analogous components throughout the several views.

DETAILED DESCRIPTION OF THE DRAWINGS

Ultrasound Eye Scanning Apparatus

Figure 1:
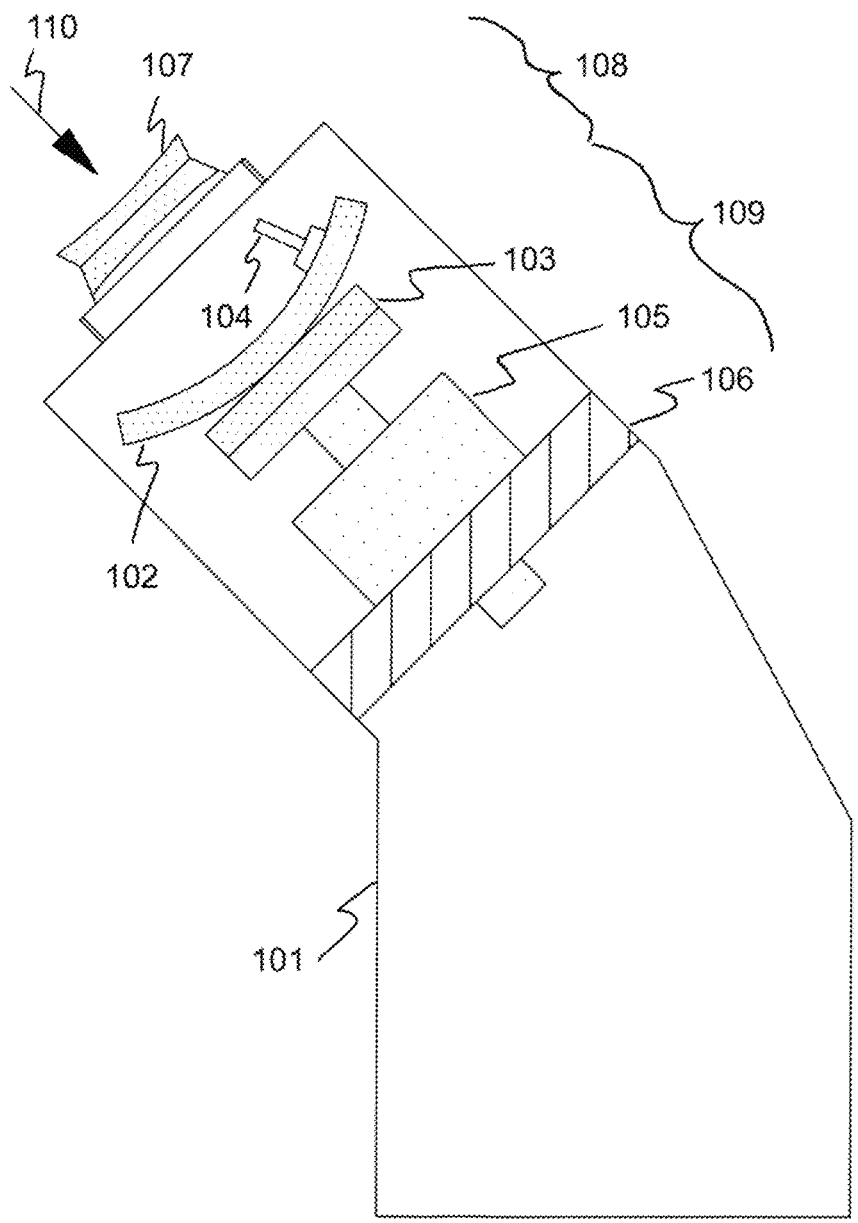
FIG. 1 is a schematic of the principal elements of a prior art ultrasound eye scanning device.

FIG. 1 is a schematic of the principal elements of a prior art ultrasound eye scanning device such as described in U.S. Pat. No. 8,317,709, entitled "Alignment and Imaging of an Eye with an Ultrasonic Scanner". The scanning device 101 of this example is comprised of a disposable eyepiece 107, a scan head assembly 108 and a positioning mechanism 109. The scan head assembly 108 is comprised of an arcuate guide 102 with a scanning transducer 104 on a transducer carriage which moves back and forth along the arcuate guide track 102, and a linear guide track 103 which moves the arcuate guide track 102 back and forth (as described further in FIG. 3). The positioning mechanism 109 is comprised of an x-y-z and beta mechanisms 105 (described in FIG. 4) mounted on a base 106. The base 106 is rigidly attached to the scanning device 101. A longitudinal axis 110 passes generally through a center of the head assembly 108 and is substantially perpendicular to a face of the eyepiece 107. A video camera (not shown) may be positioned within the scanning device 101 and aligned with the longitudinal axis 110 to provide an image of a patient's eye through the eyepiece 107. The scanning device 101 is typically connected to a computer (not shown) which includes a processor module, a memory module, a keyboard, a mouse or other pointing device, a printer, and a video monitor. One or more fixation lights (not shown) may be positioned within the scanning device at one or more locations. The eyepiece 107 is designed to be disposable.

The positioner assembly 109 and scan head assembly 108 are both fully immersed in water (typically distilled water) which fills the chamber from base plate 106 to the top of the chamber on which the eyepiece 107 is attached.

A patient is seated at the scanning device 101 with one eye engaged with the disposable eyepiece 107. The patient is typically directed to look downward at one of the fixation lights during a scan sequence. The patient is fixed with respect to the scanning device 101 by a headrest system such as shown, for example, in FIG. 2, and by the eyepiece 107.

An operator using a mouse and/or a keyboard and the video monitor, for example, inputs information into the computer selecting the type of scan and scan sequences as well as the desired type of output analyses. The operator using the mouse and/or the keyboard, the video camera located in the scanning machine, and the video screen, centers a reference marker such as, for example, a set of cross hairs displayed on the video screen on the desired component of the patient's eye which is also displayed on video screen. This is done by setting one of the cross hairs as the prime meridian for scanning. These steps are carried out using the positioning mechanism which can move the scan head in the x, x, z and beta space (three translational motions plus rotation about the z-axis). The z-axis is parallel to the longitudinal axis 110. Once this is accomplished, the operator instructs the computer to proceed with the scanning sequence. Now the computer processor takes over the procedure and issues instructions to the scan head 108 and the scanning transducer 104 and receives positional and imaging data. The computer processor proceeds with a sequence of operations such as, for example: (1) with the transducer carriage substantially centered on the arcuate guide track, rough focusing of the scanning transducer 104 on a selected eye component; (2) accurately centering of the arcuate guide track with respect to the selected eye component; (3) accurately focusing the scanning transducer 104 on the selected feature of the selected eye component; (4) rotating the scan head assembly 108 through a substantial angle (including orthogonal) and repeating steps (1) through (3) on a second meridian; (5) rotating the scan head back to the prime meridian; (6) initiating a set of A-scans along each of the of selected scan meridians, storing this information in the memory module; (7) utilizing the processor, converting the A-scans for each meridian into a set of B-scans and then processing the B-scans to form an image associated with each meridian; (8) performing the selected analyses on the A-scans, B-scans and images associated with each or all of the meridians scanned; and (9) outputting the data in a preselected format to an output device such as a printer. As can be appreciated, the patient's head must remain fixed with respect to the scanning device 101 during the above operations when scanning is being carried out, which in a modern ultrasound scanning machine, can take several tens of seconds.

An eyepiece serves to complete a continuous acoustic path for ultrasonic scanning, that path extending in water from the transducer to the surface of the patient's eye. The eyepiece 107 also separates the water in which the patient's eye is immersed (typically a saline solution) from the water in the chamber (typically distilled water) in which the transducer guide track assemblies are contained. The patient sits at the machine and looks down through the eyepiece 107 in the direction of the longitudinal axis 110. Finally, the eyepiece provides an additional steady rest for the patient and helps the patient's head to remain steady during a scan procedure.

Figure 2:
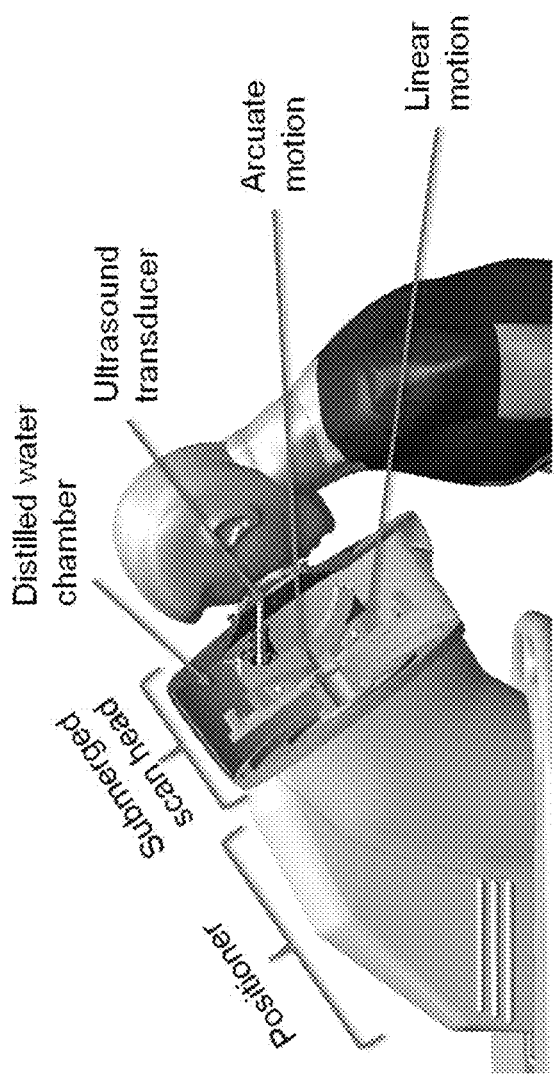
FIG. 2 is a schematic cutaway drawing of an arc scanner.
Figure 4:
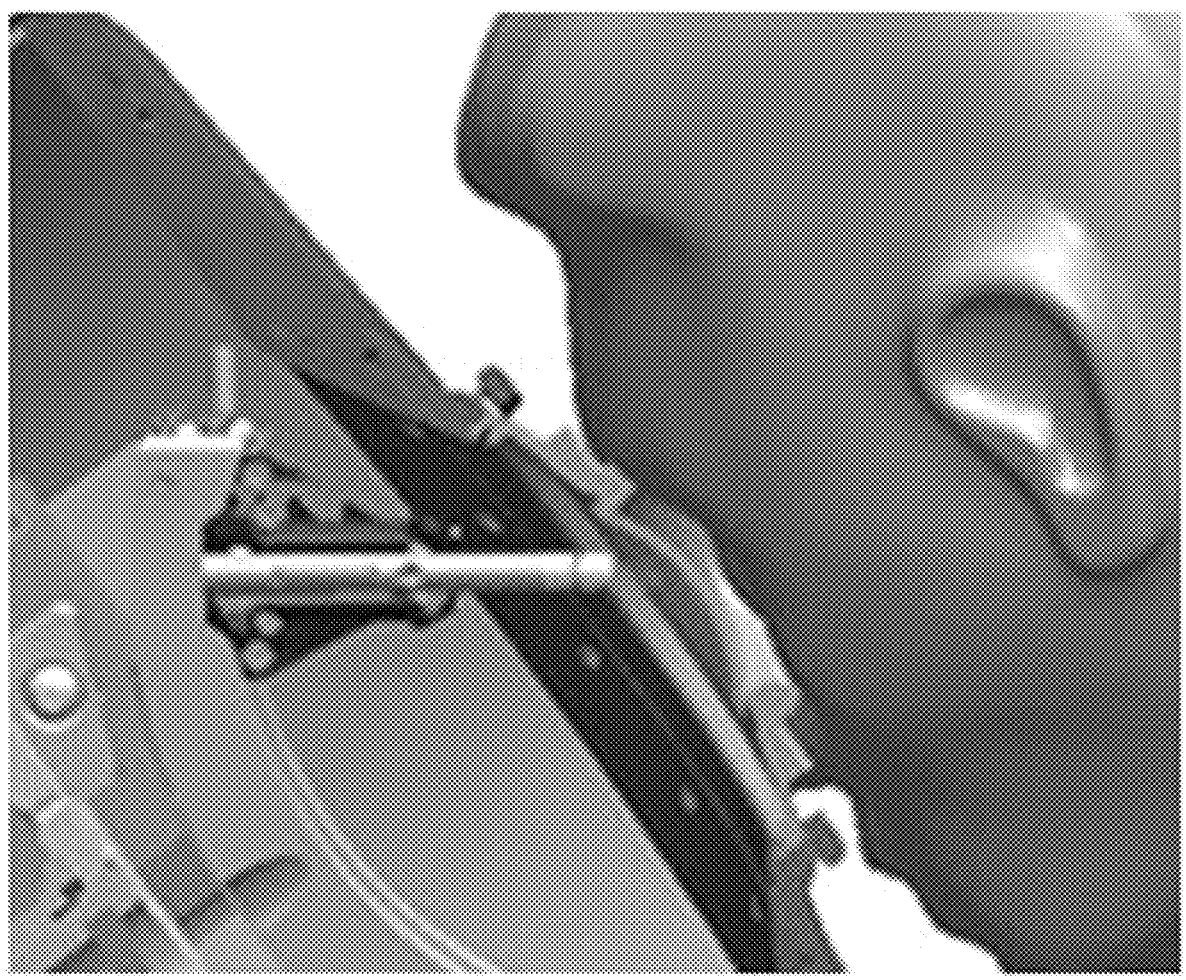
FIG. 4 is a cutaway view of a prior art arc scanning device with patient in position for scanning.

FIG. 2 is a schematic cutaway drawing of an arc scanner. The scan head is immersed in distilled water within a bucket (shown in cut away view). The bucket is attached to and separated from a housing which contains the instrument electronics and the positioner mechanism. The housing is open to ambient air. A telescoping shaft of the positioner mechanism goes through a large, flexible sealing membrane into the bucket and the scan head is attached to the immersed end of this shaft. The scan head comprises a linear track on which is mounted an arcuate track. An ultrasound transducer is mounted on a carriage which can move along the arcuate track. In FIG. 4, a patient is shown with one eye pushed against an eye piece.

Figure 3:
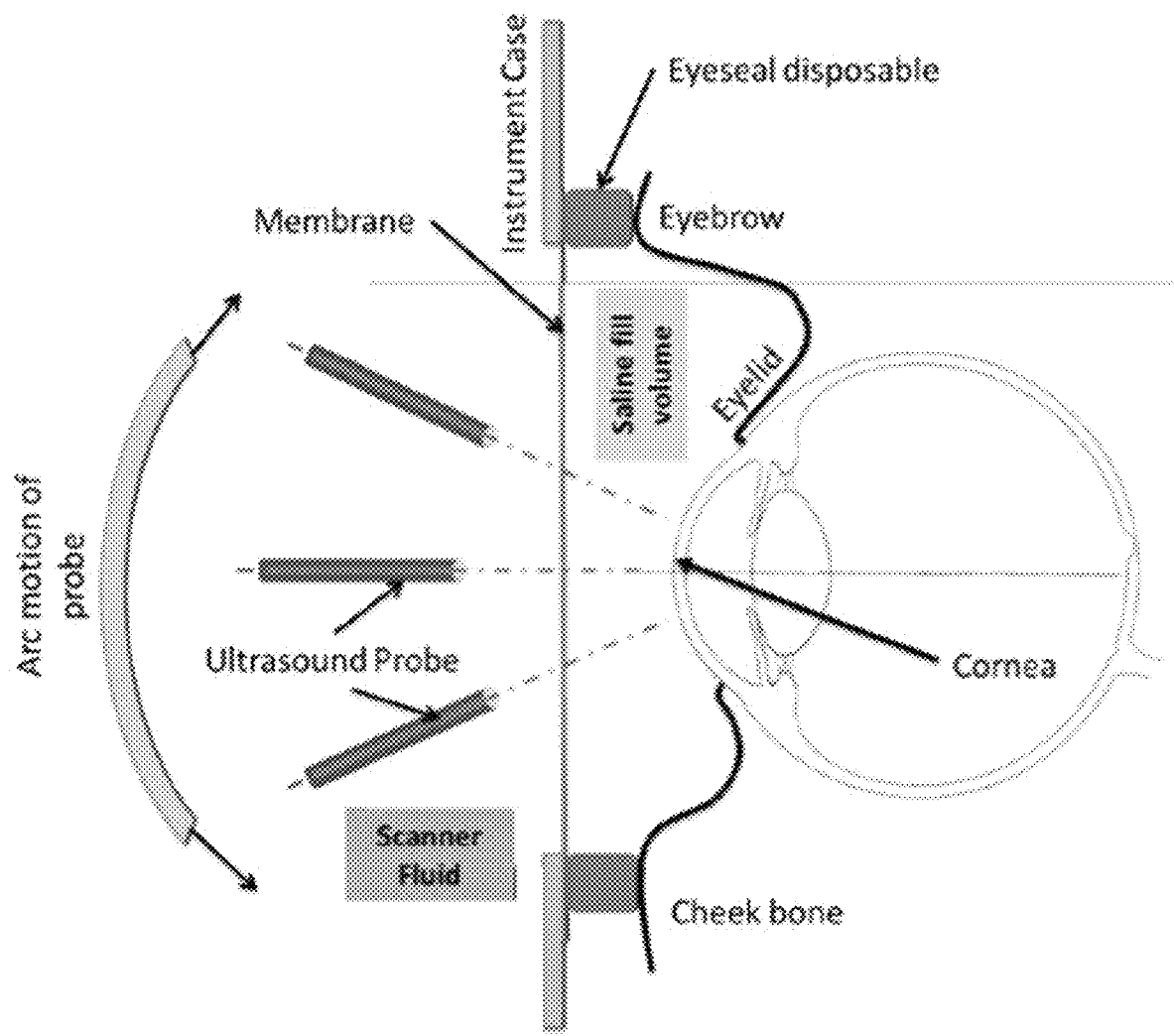
FIG. 3 is a further schematic representation of an arcuate scan.

FIG. 3 is a further schematic representation of an arc scanning device. This figure illustrates the relation between the arcuate track, the ultrasound probe shown in different positions in time, the eye piece membrane, the soft flexible sealing ring of the eye piece and the patient's eye as positioned for scanning. The arcuate track and ultrasound probe are immersed in distilled water (shown here as scanner fluid). The front of the patient's eye is immersed in saline fluid which fills the eye piece once the patient's eye seals against the soft flexible sealing ring of the eye piece.

A sealed hygienic barrier or membrane separates the distilled water from the saline solution. As can be appreciated, the eye piece and saline fluid is changed for each patient. The saline fluid is usually changed between separate scanning sessions for each patient.

FIG. 4 is a cutaway view of a prior art arc scanning device with patient in position for scanning. FIG. 4 shows the features of FIG. 3 in a more realistic representation. The patient's eye is pressed against the soft flexible sealing ring of the eye piece which is now attached to the mounting ring which, in turn, is attached to the main scanner housing as described in FIG. 5. An ultrasound probe is shown at the top end of the arcuate guide track and is aimed at the patient's eye. As the probe moves along the arcuate guide track, its long axis remains approximately perpendicular to the surfaces of the cornea and anterior lens of the patient's eye. The term approximately can mean a variation of +/−10% on a relative basis. The tip of the ultrasound transducer comes very close to the membrane that separates the distilled water in the instrument bucket from the saline solution in the eye piece. The transducer is attached to the transducer carriage by small magnets which will release the probe if it contacts the membrane with enough force to endanger the patient's eye.

Figure 5:
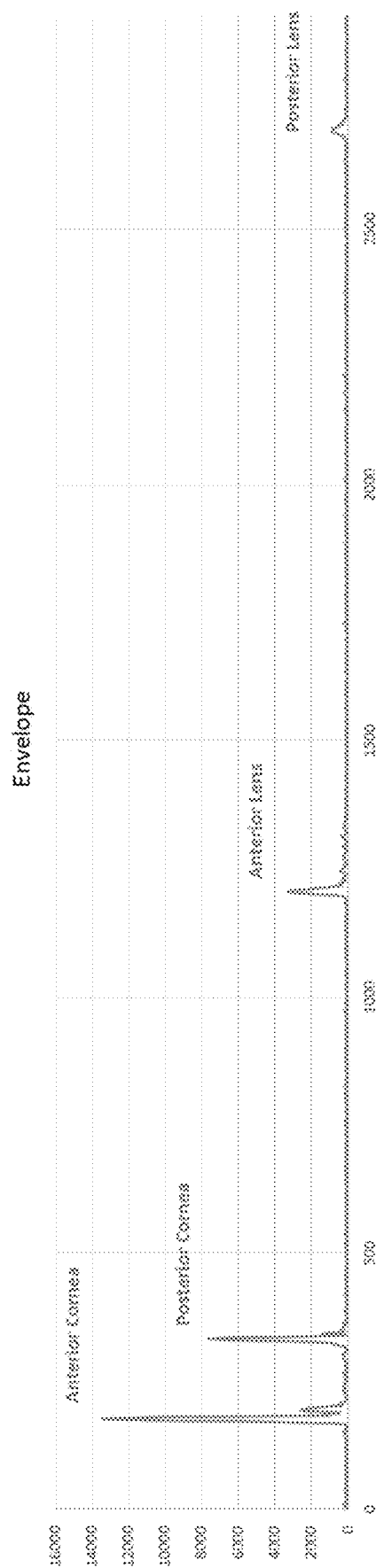
FIG. 5 is an envelope of an A-scan of the anterior segment of an eye recorded near the visual axis of an eye.

FIG. 5 is an envelope of an A-scan of the anterior segment of an eye recorded near the visual axis of an eye. The envelope is obtained by doing a Fourier transform of the A-scan, removing the negative frequency components and then doing an inverse Fourier transform to obtain the envelope. Alternately, the envelope can be obtained by using the Hilbert function. In either procedure, the envelope is the magnitude of the analytic signal which captures the slowly varying features of the A-scan signal, while the phase contains the high-frequency information.

FIG. 5 shows the location of the specular surfaces of the anterior and posterior cornea and lens which are taken as the local maxima of their respective peaks.

The abscissa is in units of sample number where each sample interval represents 2.5 nanoseconds which corresponds to the 250 MHz A/D converter currently being used. The ordinate is in units of bits corresponding to those of the 16-bit A/D converter.

Figure 6:
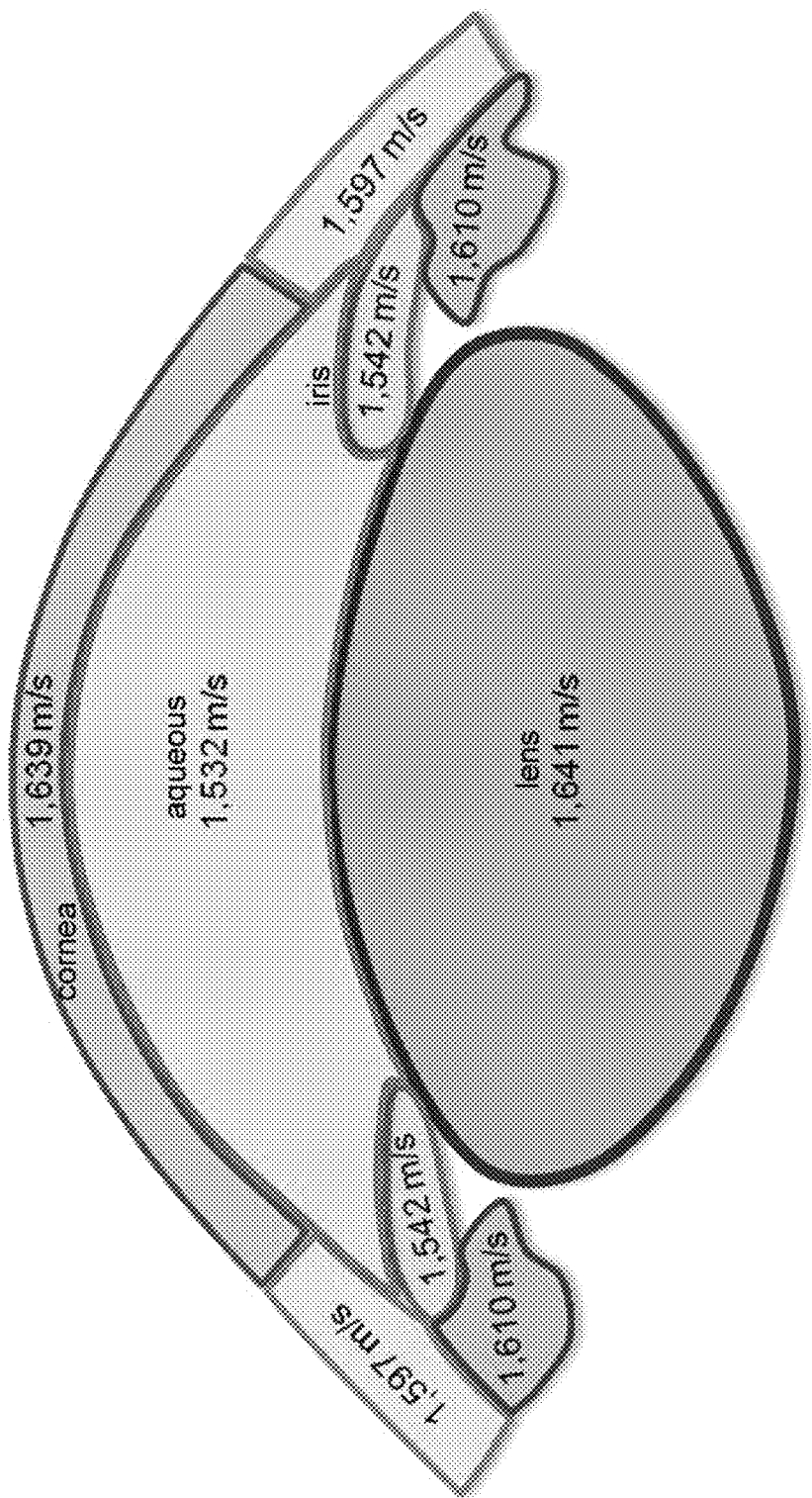
FIG. 6 is a schematic of an eye showing sound speeds for various regions in the anterior segment.

FIG. 6 is a schematic of an eye showing sound speeds for various regions in the anterior segment. The best estimate values for each region, taken from "Ultrasonography of the Eye and Orbit", Second Edition, Coleman et al, published by Lippincott Williams & Wilkins, 2006 which is incorporated herein by reference, are shown for the cornea, aqueous fluid, lens, iris and sclera. These values may be updated when more accurate data become available. For example, it is possible to measure the speed of sound for each region using a method such as described in U.S. Pat. No. 9,149,254 entitled "Alignment and Imaging of an Eye with an Ultrasonic Scanner", which was referenced previously. Cadaver eyes may be implanted with metallic pins of a known separation and scanned by a precision ultrasound scanner to obtain speed of sound estimates in various components of an eye.

Figure 7:
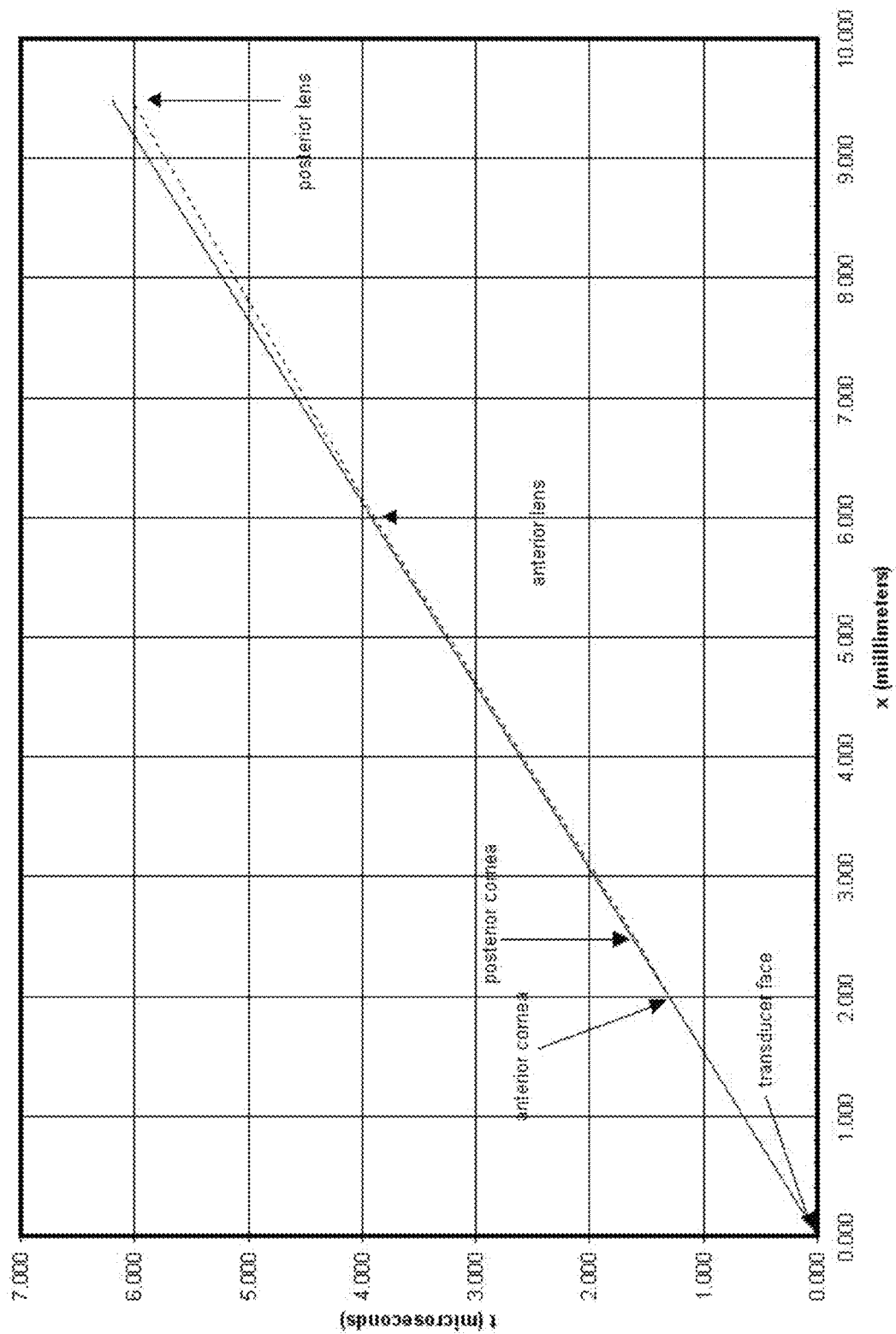
FIG. 7 is a time-distance plot for an ultrasound pulse propagated in the anterior segment of an eye.

FIG. 7 is a time-distance plot for an ultrasound pulse propagated in the anterior segment of an eye. This figure illustrates the effect of choosing a known speed of sound for each region as opposed to using an average speed of sound for all regions. The dashed line represents the times of arrival at region interfaces when a known speed of sound is used for each region. The solid line represents the times of arrival when an average speed of sound is used for all regions. As can be seen, significant errors can result for regions such as the natural lens (whose time-of-arrivals are relatively large).

As an example, the transit time across the lens is 2.29 microseconds assuming a speed of sound of 1,531 m/s. The transit time across the lens is 2.13 microseconds assuming a known speed of sound for the natural lens of 1,641 m/s. This 0.263 microsecond difference is approximately equivalent to a distance error of about 0.263 millimeters or 263 microns. Using an average sound speed rather than a known sound speed to measure lens depth would result in about a 7.5% error in measured lens depth. This would be a significant error in determining the power of a lens replacement for example.

As another example, the transit time across the cornea is 0.3266 microseconds assuming a speed of sound of 1,531 m/s. The transit time across the cornea is 0.3051 microseconds assuming a known speed of sound for the natural lens of 1,639 m/s. This 0.0215 microsecond difference is approximately equivalent to a distance error of about 35 microns. Using an average sound speed rather than a known sound speed to measure cornea thickness would result in about a 7% error in measured cornea thickness. This would be a significant error in determining the depth of a LASK cut for example.

In actual scanning, the times-of-arrival are known. The times at which each A-scan intersects an interface are the times measured at the interfaces as determined from the envelope of each A-scan.

Figure 8:
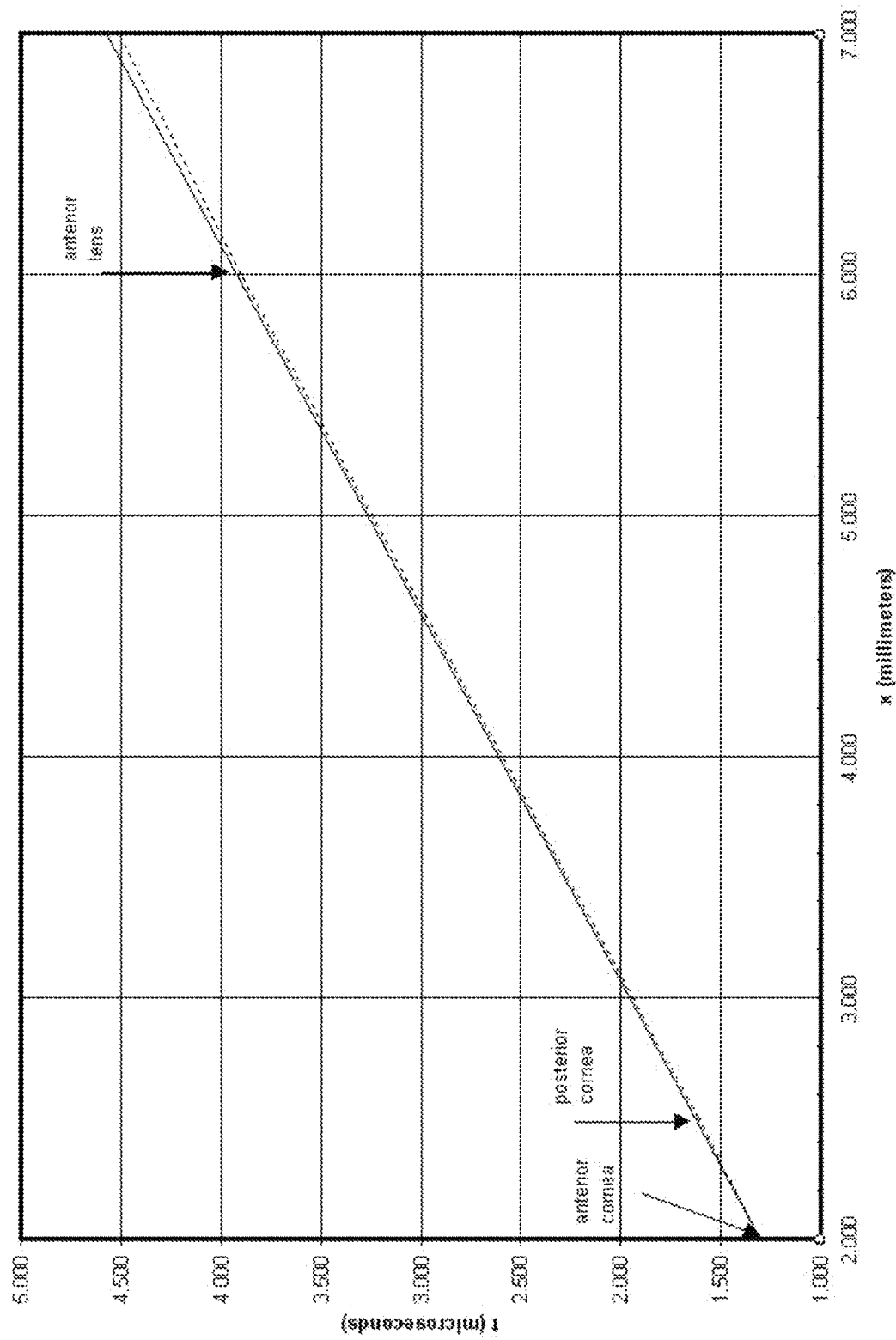
FIG. 8 is a close-up of the time-distance plot of FIG. 14.

FIG. 8 is a close-up of the time-distance plot of FIG. 7. The dashed line represents the times of arrival at region interfaces when a known speed of sound is used for each region. The solid line represents the times of arrival when an average speed of sound is used for all regions. As can be seen, significant errors can result for regions such as the natural lens (whose time-of-arrivals are relatively large).

Figure 9:
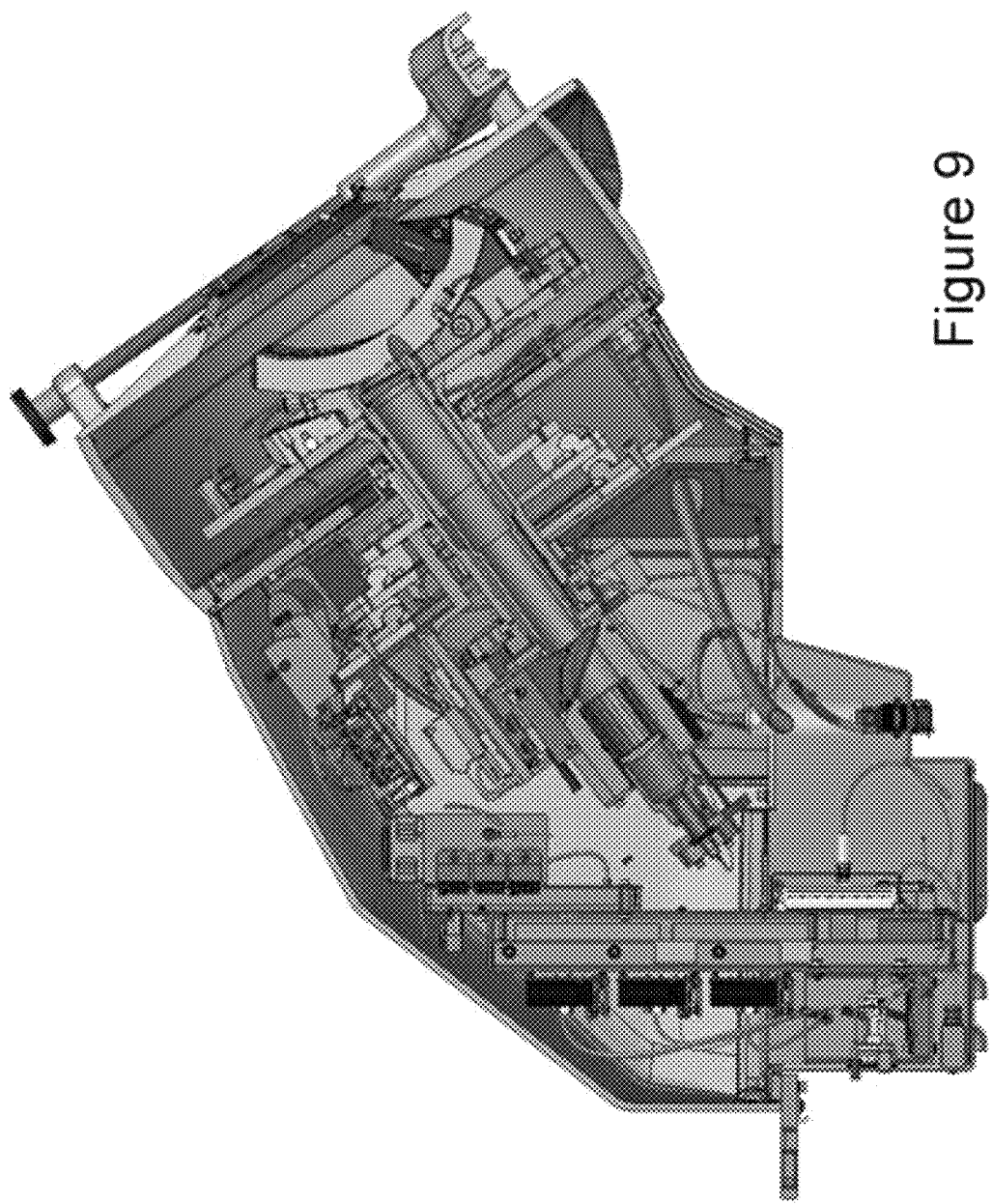
FIG. 9 is a cutaway drawing of an arc scanning instrument.

FIG. 9 is a cutaway drawing of an arc scanning instrument. This rendering shows more detail than the rendering of FIG. 4. The scan head, which includes the transducer carriage and ultrasound transducer, is shown inside its bucket housing. The scan head is shown attached to one end of a positioner mechanism. The positioner mechanism extends from the rear housing, through a flexible rubber membrane into the bucket housing.

As discussed previously, the bucket housing is filled with distilled water for scanning. The rear housing is kept at ambient air conditions and typically has a fan or fans to circulate air within the rear housing.

The distilled water is circulate through the bucket housing to provide water for the fluid bearings for the scan head arcuate and linear guide tracks. This water carries heat into the bucket housing and heats the water in the bucket housing.

The bucket housing is separated from the rear housing by an aluminum plate (which includes the flexible rubber membrane mentioned above). Heat from the water in the bucket housing conducts through the aluminum plate and heats the air in the rear housing. The heated air in the rear housing is then blown out of the housing by several fans. It is also possible to discard heat from the water in the bucket housing by circulating the water through cooling coils or other means.

Figure 10:
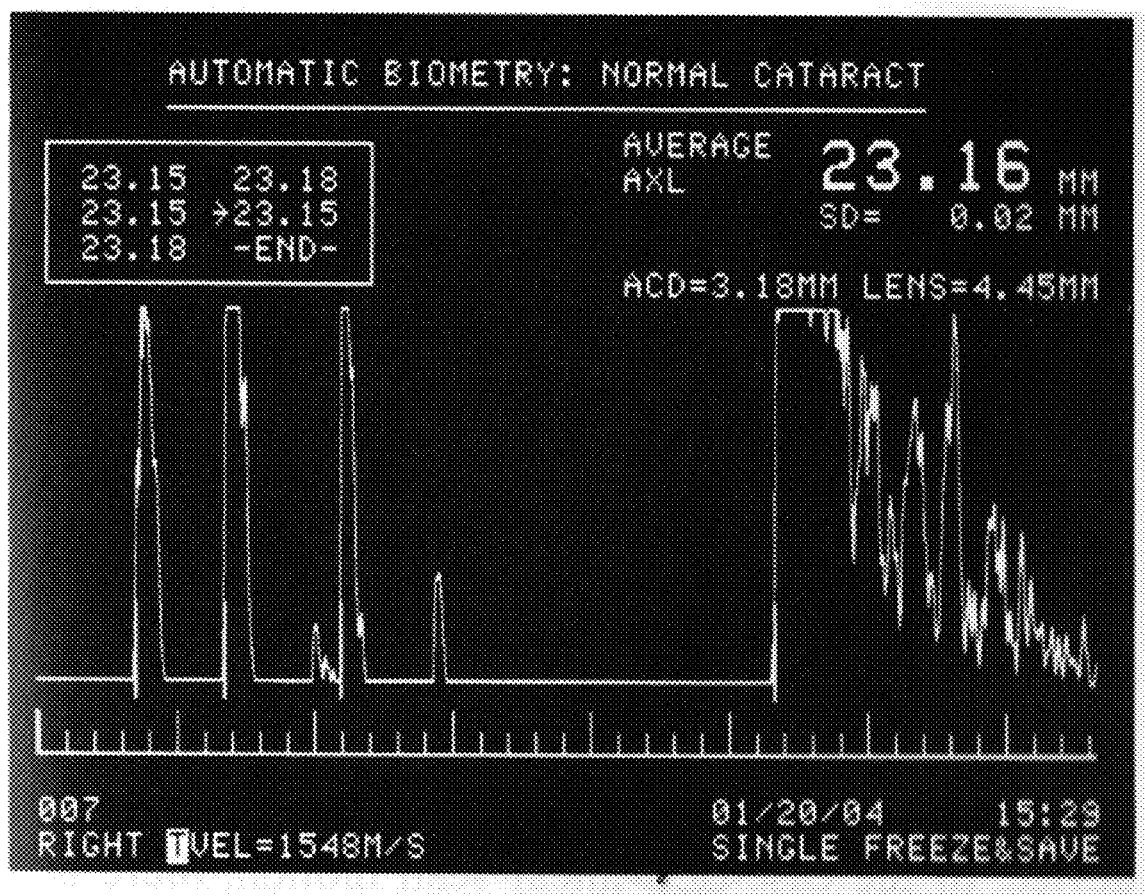
FIG. 10 is an envelope of an A-scan of a cornea recorded near the visual axis of an eye.

FIG. 10 shows a typical A-scan recorded near the visual axis of an eye. FIG. 10 illustrates a received signal waveform from signal reflections within the anterior segment. This figure illustrates a typical A-scan and was taken from "Ultrasonography of the Eye and Orbit" which was referenced previously. An A-scan is the electronically recorded amplitude-time history of a reflected acoustic pulse received by the arc scanner's transducer. An unprocessed A-scan is shown as signal amplitude in volts versus time in microseconds. Typically an A-scan is displayed to the ultrasound scanner operator as a rectified trace with signal amplitude in volts versus time in microseconds. In addition to being rectified, the A-scan trace may also be filtered to remove unwanted thermal and electronic noise.

Figures 11A, 11B, 11C:
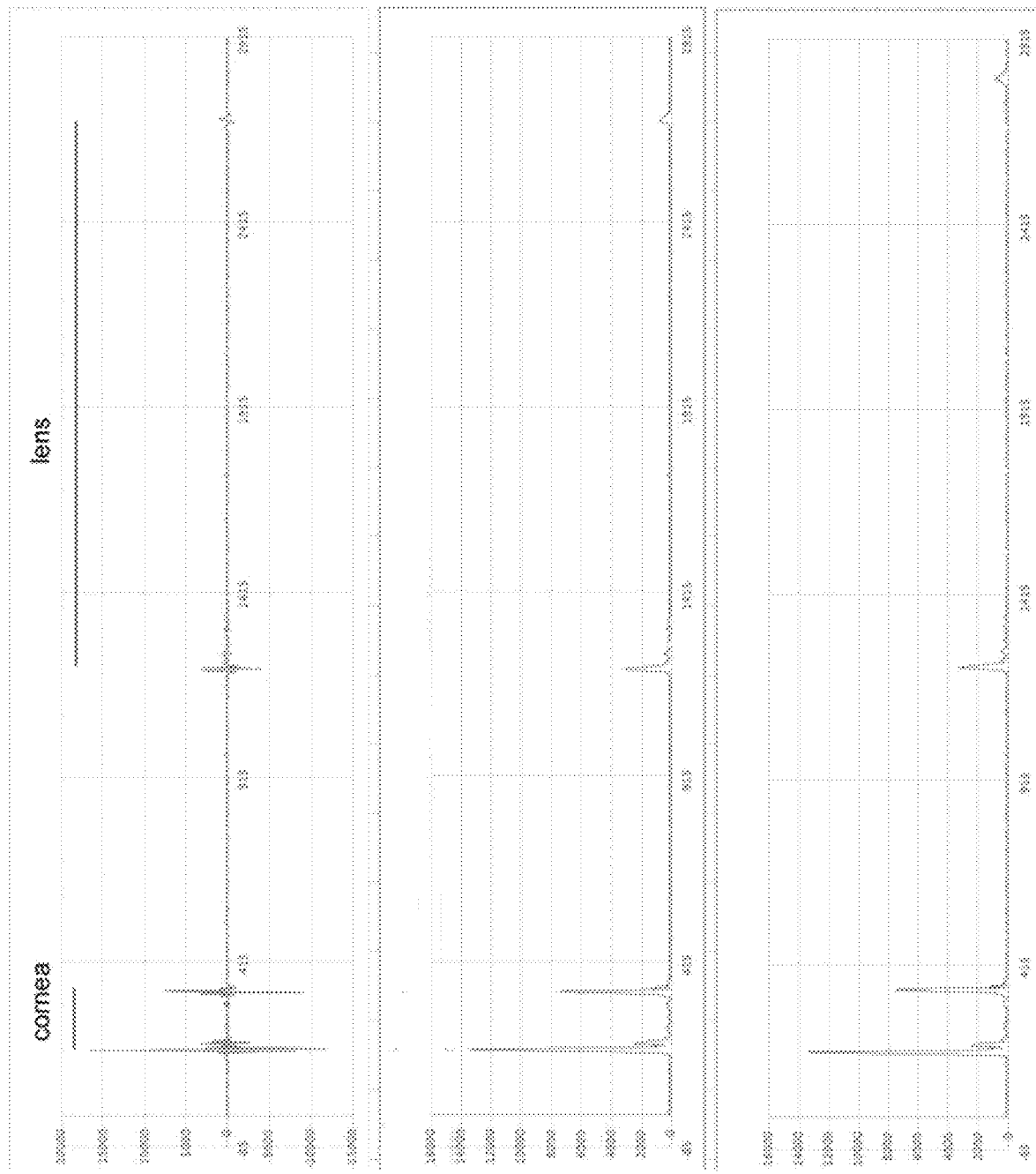
FIGS. 11a, 11b and 11c show an A-scan, its envelope and its corrected envelope.

FIGS. 11a, 11b and 11c show an A-scan, its envelope and its corrected envelope. FIG. 11a is a trace of an A-scan. FIG. 11b is the envelope of the A-Scan trace of FIG. 11a. FIG. 11c is the converted envelope wherein the abscissa is now position, having been corrected for speed of sound estimates in the cornea, aqueous fluid and lens.

The abscissa of FIGS. 11a and 11b is in units of sample number where each sample interval represents 2.5 nanoseconds which corresponds to the 250 MHz A/D converter currently being used. The ordinate is in units of bits corresponding to those of the 16-bit A/D converter.

In each of FIGS. 11a, 11b and 11c, the depth of the cornea and the depth of the lens are indicated by black horizontal lines. The depth of the cornea is about 150 sample intervals or about 375 nanoseconds (or about 0.615 mm using a speed of sound of 1,639 m/s). The depth of the aqueous fluid is about 875 sample intervals or about 2,187.5 nanoseconds (or about 3.35 mm using a speed of sound of 1,532 m/s). The depth of the lens is about 1,500 sample intervals or about 3,750 nanoseconds (or about 6.16 mm using a speed of sound of 1,641 m/s).

Image Types and Scan Types

An image type is a B-scan of, for example, a cornea image, an anterior segment image, a lens capsule image or a composite of image types.

A scan type is a specific set of transducer motions such as, for example, an arcuate scan of the same radius of curvature as the arcuate guide track, a linear scan, an arcuate scan of a selected radius of curvature which can be obtained by a combined motion of the arcuate and linear scan mechanisms.

Possible Transducer Motions

The transducer moves in an x-y-z beta co-ordinate system.

The x-y movements are used in positioning for centering on the eye. The x-y positions are monitored by a magnetic encoder strip to a resolution of about 5 microns.

The z movement is used in positioning for range finding of a patient's eye (setting the focal depth of transducer). The z position is monitored by its own magnetic encoder strip to a resolution of about 5 microns.

The beta angle sets the meridian for the scan and is monitored by its own magnetic encoder strip to an angular resolution of about 0.09 degrees.

The transducer can be further oriented and positioned by moving the transducer carriage along the arcuate track. Position of the transducer on its carriage along the arcuate guide track is monitored by its own magnetic encoder strip to a resolution of about 1 micron.

The arcuate track can be further positioned by moving the arcuate track along the linear guide track which is also monitored by its own magnetic encoder strip to a resolution of about 1 microns.

These various possible motions can be used individually or combined to form the various scan types wherein each scan type is aimed at generating a desired image.

For example, a cornea scan is generated by moving the transducer along the acuate guide track with a radius of curvature of about 10 mm to produce an image of the cornea which generally includes the epithelium, Bowman's layer, the stroma and the endothelium.

As another example, an anterior segment scan is generated by moving the transducer along the acuate guide track with a selected radius of curvature between about 10 mm and about 20 mm which is achieved by using a combination of transducer carriage movement along the arcuate guide track and arcuate guide track movement along the linear guide tract wherein both movements are in the same direction. This scan produces an image of the cornea, the aqueous region and at least the anterior surface of the lens capsule. This scan usually also shows a short section of the posterior lens near the visual axis. This short section of the posterior lens can be used for registration purposes when compositing images.

As another example, a central posterior capsule scan is generated by moving the transducer to optimize the orientation of the transducer to remain substantially normal to the posterior capsule surface using a combination of transducer carriage movement along the arcuate guide track and arcuate guide track movement along the linear guide tract wherein the two movements are in opposing directions. This scan produces an image of the central posterior lens surface.

As another example, a left and right segment of the posterior capsule scan is generated by fixing the position of the transducer on the arcuate guide track at a selected angle to the visual axis and moving the arcuate guide track along the linear guide tract. This scan produces images of a short section of the posterior lens surface to the left and right of the central portion of the lens surface.

The above scans can be done in rapid succession under computer control and then composited into a single image, also under computer control.

Other, more specialized scan types are possible. For example, the region of the eye around the iridocorneal angle and the scleral spur can be imaged by a series of scans wherein each scan is generated by moving the y-positioner a short distance then indexing by about 50 microns using the x-positioner and then repeating moving the y-positioner a short distance.

Another example of a specialized scan type is moving the transducer in a tight radius arc, then moving the transducer in a series of offset radius arcs. These types of scan can generate a series on images of the equatorial region of the lens capsule which can then be composited with other images of various sections of the posterior lens capsule.

As can be appreciated, other scan types can be created by prescribing coordinated movements of the positioner mechanism, the scan head and the transducer carriage.

Determining an Eye Component Surface

The following steps are typically used to determine quantitatively the positions of the various eye component surfaces (anterior and posterior of the cornea and lens) in an appropriate co-ordinate system such as x-y-z with respect to the arcuate guide track center of curvature when the linear guide track is in a fixed position:
  7. Do a scan and generate an array of A-scans
  8. Calculate the envelope of each A-scan in the array
  9. Convert envelope volts to grayscale and the envelope intervals to time
  10. Using an appropriate sound speed, convert envelope time to distance
  11. Determine the position of each A-scan in the selected co-ordinate system (such as x-y-z with respect to the arcuate guide track center of curvature when the linear guide track is in a fixed position)
  12. Create a B-can plotting grayscale amplitude versus x-z position
  13. For each A-scan envelope, find the position of the local maximum grayscale values corresponding to the anterior and posterior of the surfaces of the cornea and lens
  14. Plot these local maxima as the specular surfaces of the anterior and posterior of the cornea and lens As can be appreciated, other surfaces may be determined in the same way. For example, the epithelial thickness, Bowman's layer, stroma thickness and endothelial thickness of the cornea can be determined. If LASIK has been performed on the patient, an image of LASIK flap can be generated on the B-scan.

Imaging the Equator of the Natural Lens Capsule

Figure 12:
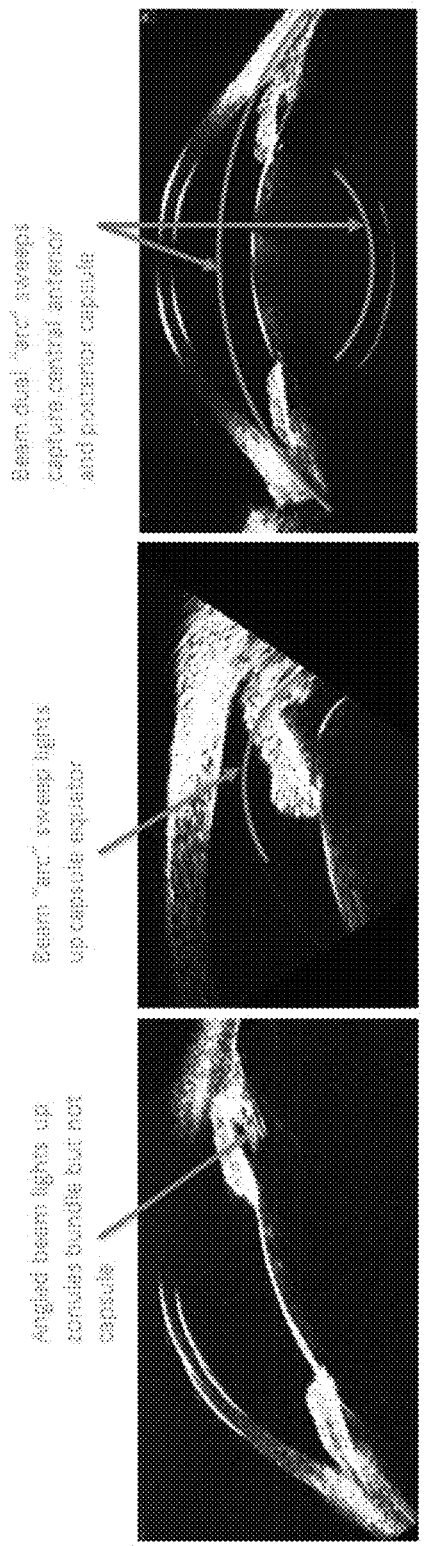
FIG. 12 illustrates a method of imaging the equatorial diameter of a lens.

FIG. 12 illustrates a method of imaging the equatorial diameter of a lens. In FIG. 12, a computer controls an ultrasound beam path by positioning the transducer probe in preparation for emitting an ultrasound pulse. A scan head combines two degrees of freedom: a combined arcuate and linear motion allows for optimized imaging trajectory to image a particular feature within the anterior segment of an eye.

The closer the emitted ultrasound pulse is to perpendicularity with the interface it encounters, the stronger the reflected signal that is returned. An arcuate track of approximately the radius of curvature as the cornea returns a strong signal from the anterior and posterior cornea and also returns a strong signal from much of the anterior lens surface. A measurable signal can be returned from the pole of the posterior lens surface. As is well known, other factors affecting the return signal strength are attenuation from total round trip signal travel distance and type of tissue encountered (scleral tissue attenuates more than corneal tissue or aqueous fluid). But it has always been difficult to obtain a measurable reflected signal from the capsule ends on the equatorial diameter of the lens capsule because this region of the lens capsule is closer to parallel to the ultrasound beam than perpendicular.

As discussed previously, the radius of curvature along which the transducer tip moves with respect to the patient's eye can be varied by a prescribed combination of transducer motion as the transducer carriage moves along the arcuate guide track and the scan head moves along the linear guide track.

When the transducer carriage moves along the arcuate guide track and the scan head moves in the same direction along the linear guide track, a larger radius of curvature than that of the arcuate guide track results. When the transducer carriage moves along the arcuate guide track and the scan head moves in the opposite direction along the linear guide track, a smaller radius of curvature than that of the arcuate guide track or an inverse radius of curvature results. A scan with an inverse radius of curvature will return an image of a substantial portion of the posterior lens surface but generally not the equatorial ends of the capsule.

FIG. 12 illustrates a method of imaging the equatorial diameter of a lens wherein:
  1. the eye is dilated (dilation changes the eye dimensions somewhat but, more than offsetting this effect, dilating prevents the eye from accommodating as the light changes entering the patient's eye during scanning)
  2. the eye is rotated (rotation changes the eye dimensions somewhat but, more than offsetting this effect, rotating results in less signal attenuation)
  3. a number of small constant positive radius of curvature scans is prescribed As can be seen from FIG. 12, this results in scan sweeps that allow the emitted pulse to reflect from the end of the capsule substantially perpendicular to the capsule surface near its outer equatorial diameter and also results in a reasonably short round trip travel through a minimum of scleral tissue.

Normally, a particular scan is made with a constant radius of curvature but the radius of curvature that can be changed from scan to scan. It is also possible to prescribe a variable radius of curvature during a scan by the appropriate combination of arcuate transducer carriage and linear scan head motion trajectories.

Figure 13:
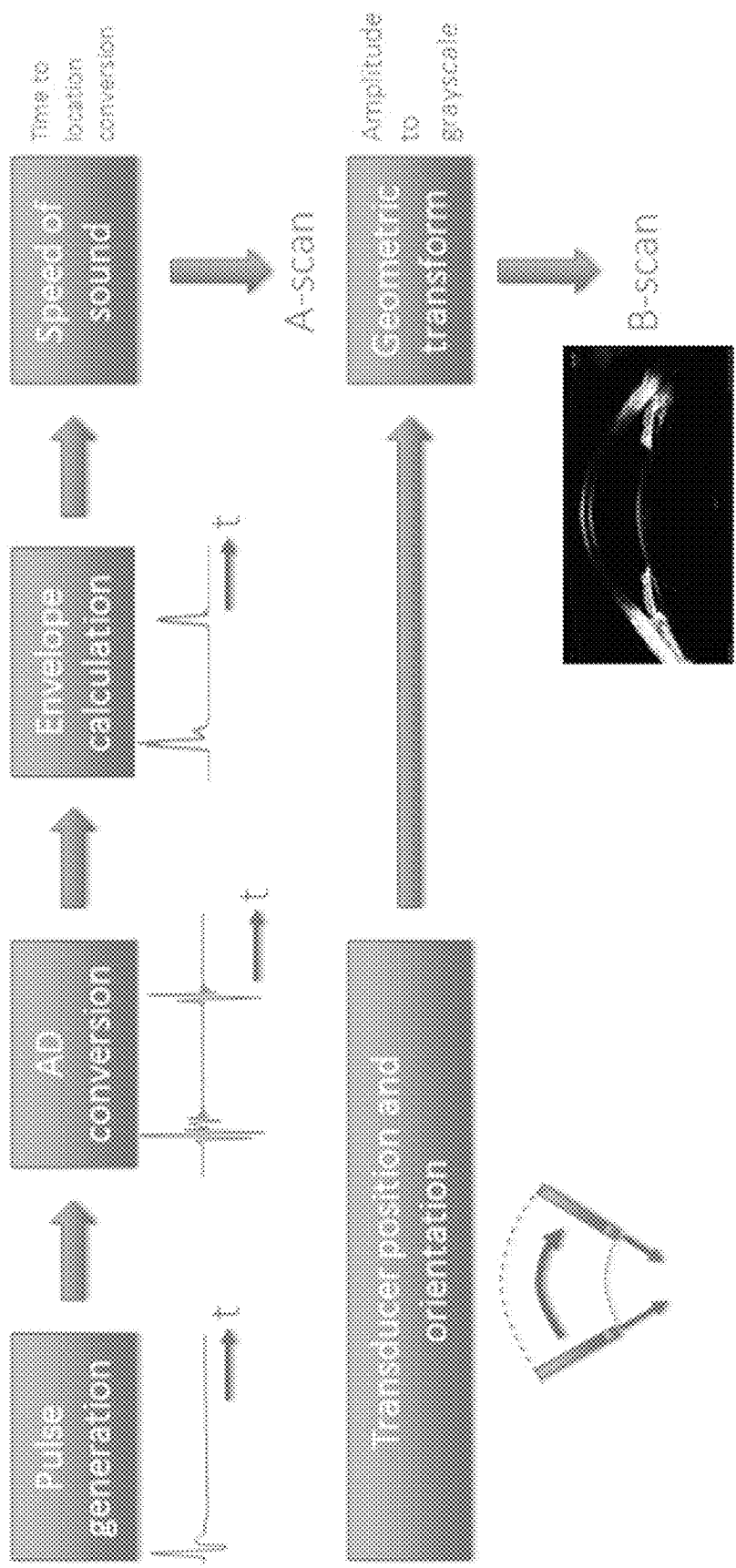
FIG. 13 shows the main steps to form a B-Scan.

FIG. 13 shows the main steps to form a B-Scan. These are:
  1. Generate an outgoing ultrasound pulse from an ultrasound transducer. The outgoing pulse reflects off a specular surface of an eye component and the reflected pulse is subsequently received by the ultrasound transducer. The ultrasound transducer forms an analogue electrical signal of an A-scan (volts versus time).
  2. The transducer position and probe orientation are recorded for each emitted ultrasound pulse.
  3. The analogue signal is converted to a digital signal (volts versus time) by an A/D converter.
  4. The envelope of the digital signal (positive volts versus time) is formed by an inverted Fast Fourier Transform (FFT).
  5. The envelope is converted to a volts versus distance signal by applying the speed of sounds for each region of the eye that the signal has passed through.
  6. The amplitude of the envelope is then transformed into the final B-scan using a gray scale algorithm that assigns black to zero voltage and lighter shades to the higher voltages.

Formation of a Composite B-Scan Image

Typically, an arc scanner can produce several different types of scans. These include, for example, an arcuate scan, a linear scan or scans of various radii of curvature including inverse radii of curvature. Each type of scan is taken at slightly different times and in between, there can be movement of the patient's eye and movement of the instrument as the transducer probe and scan head move within the instrument. In addition, intentional eye movements can be introduced to expand the range of the eye that can be imaged.

The A-scans recorded by the arc scanning instrument described herein have an amplitude range of about 32,000 samples. The envelopes of the A-scans have an amplitude range of about 16,000 samples. The A-scans have a time base range of from about 2,000 to about 4,000 equally spaced samples. In the principal steps below it is assumed the images that are to be composited have the same spatial resolution (i.e., μm/pixel). If not, one of the images needs to be resampled to match the spatial resolution of the other; typically the higher resolution is downsampled to match the lower spatial resolution.

The principal steps that are used to create a stitched or composite image are:
1. Align cornea image with the anterior segment image
   a. Pre-align the images based on transducer position on the arcuate guide track and linear guide track. The transducer positions are determined by magnetic strip encoders on the arcuate and linear guide tracks
   b. Run an optimization algorithm such as a gradient descent algorithm:
      i. Anterior image is fixed, cornea image is allowed to move
      ii. The fit metric is mean squares, the intensity difference squared averaged across all pixels between the images. Alignment is performed by reducing this value.
      iii. "Translational" transformation type; only translation in the moving image is permitted.
   c. Combine images to create a composite image such as:
      i. Set pixel intensity threshold.
      ii. If pixel has a value above the threshold in both images, average the pixels together to create the combined image.
      iii. If pixel has a value above the threshold only in one image, that value is used directly in the new image.
   d. The final image is a combined cornea/anterior image.
2. Align combined cornea/anterior image with posterior lens image
   a. Pre-align the images based on arcuate and linear guide track motor positions.
   b. Run an optimization algorithm such as the gradient descent algorithm:
      i. Anterior image is fixed, posterior lens image is allowed to move.
      ii. The fit metric is mean squares, the intensity difference squared averaged across all pixels between the images. Alignment is performed by reducing this value.
      iii. "Translational" transformation type; only translation in the moving image is permitted.
   c. Combine images to create a composite image such as:
      i. Set pixel intensity threshold.
      ii. If pixel has a value above the threshold in both images, average the pixels together in the combined image.
      iii. If pixel has a value above the threshold only in one image, that value is used directly in the new image.
   d. The final image is a full anterior image.
3. Align all equatorial capsule images
   a. Typically, 3 to 4 equatorial capsule images are captured wherein the patient's eye is rotated
   b. Pre-align the first two images based on arcuate and linear guide tracks motor positions
   c. Run an optimization algorithm such as the gradient descent algorithm:
      i. First capsule image is fixed, second capsule image is allowed to move.
      ii The fit metric is mean squares, the intensity difference squared averaged across all pixels between the images. Alignment is performed by reducing this value.
      iii. "Rigid" transformation type; rotation and translation in the moving image is permitted.
   d. Combine images to create a composite image such as:
      i. Set pixel intensity threshold.
      ii. If pixel has a value above the threshold in both images, average the pixels together in the combined image.
      iii. If pixel has a value above the threshold only in one image, that value is used directly in the new image.
   e. Repeat steps b to d for all remaining capsule images to create a single combined inferior or lower capsule image.
4. Alternatively, combining multiple registered images to create a composite image can also be performed in one step where:
   a. Set pixel intensity threshold in each image.
   b. If pixel has a value above the threshold in two or more images, average the pixels together in the combined image.
   c. If pixel has a value above the threshold only in one image, that value is used directly in the new image.
5. Align all other equatorial images capsule images
   a. Repeat step 3 for the other capsule images.
   b. This will create the other combined capsule image.
6. Align a combined equatorial capsule image with the full anterior image to extend the anterior image with the more peripheral capsule image
   a. Pre-align the combined equatorial capsule image with appropriate side of the full anterior image based on motor position and intended rotation of the eye (approximately +/−32 degrees).
   b. Run an optimization algorithm such as the gradient descent algorithm:
      i. Anterior image is fixed, combined equatorial capsule image allowed to move.
      ii. The fit metric is mean squares, the intensity difference squared averaged across all pixels between the images. Alignment is performed by reducing this value.
      iii. "Rigid" transformation type; rotation and translation in the moving image is permitted.
   c. Combine images to create a composite image such as:
      i. Set pixel intensity threshold.
      ii. If pixel has a value above the threshold in both images, average the pixels together in the combined image.
      iii. If pixel has a value above the threshold only in one image, that value is used directly in the new image.

Figure 14:
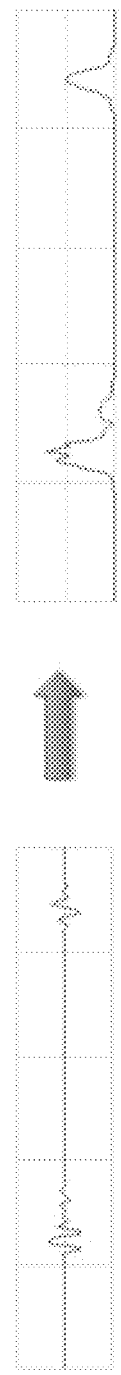
FIG. 14 illustrates additional detail for two of the steps in forming a B-Scan.
Figure 14:
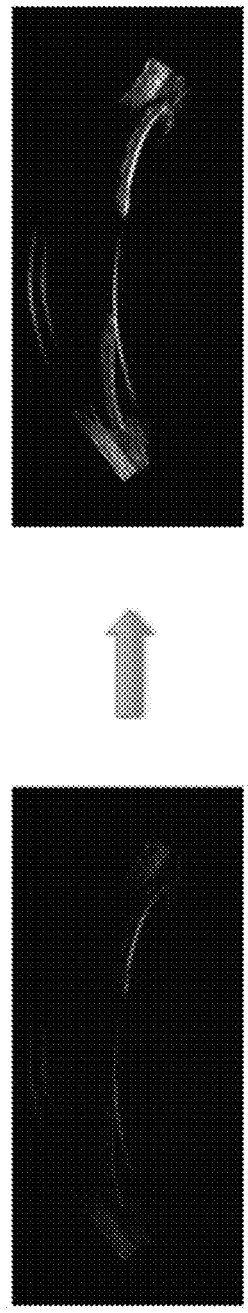
Figure 15:
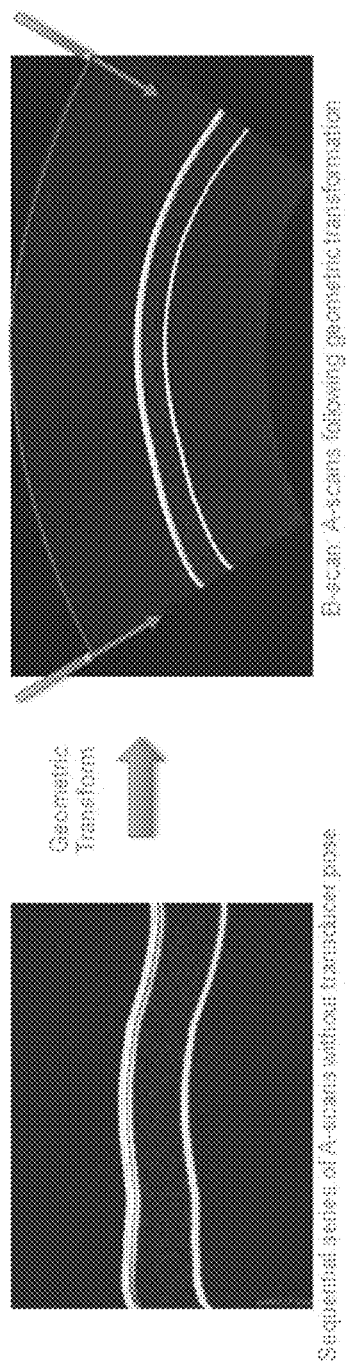
FIG. 15 illustrates additional steps in forming a B-Scan.

FIG. 14 illustrates additional detail for two of the steps in forming a B-Scan.
1. The amplitude of the envelope is then transformed into the final B-scan using a gray scale algorithm that assigns black to zero voltage and lighter shades to the higher voltages
2. The envelope is converted to a volts versus distance signal by applying the speed of sounds for each region of the eye that the signal has passed through
3. Optimize grayscale contrast for better visualization of anatomical features FIG. 15 illustrates additional steps in forming a B-Scan.
Each A-scan has a corresponding transducer position and probe orientation with about 1 micron resolution. This allows an ultrasound pulse to be positioned in space and time in an x-y-z beta co-ordinate system co-ordinate system with the origin at the intersection of the visual axis and the anterior surface of the cornea. This procedure allows multiple pulse or sweeps to be combined in a single B-scan image.

Image Processing Sequence

Figure 16:
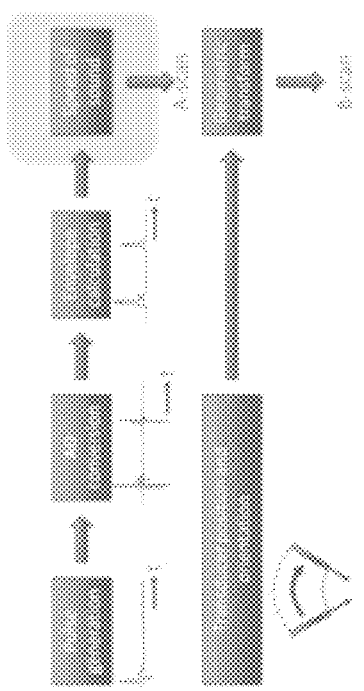
FIG. 16 demonstrates the need for correcting for speed of sound.
Figure 16:
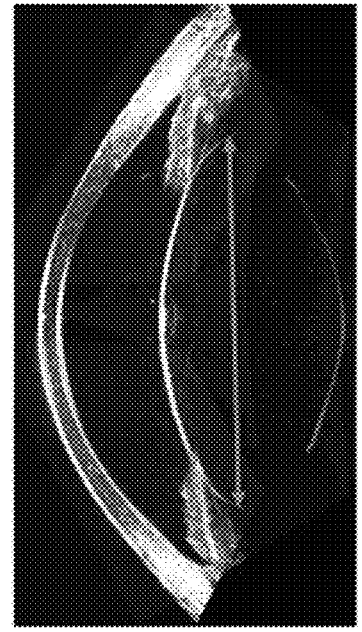
Figure 16:
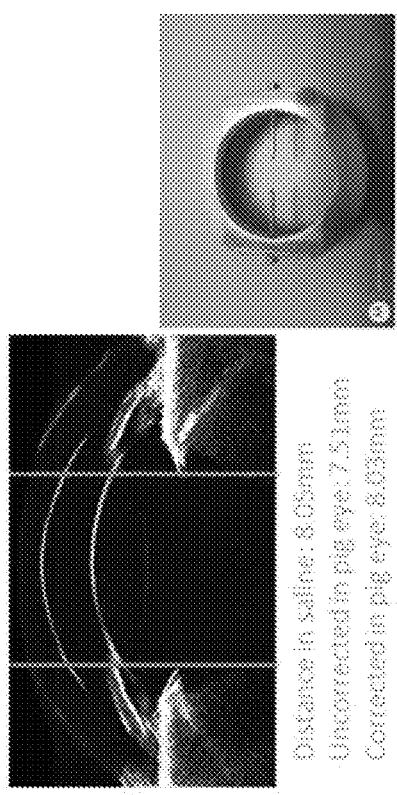
Figure 17:
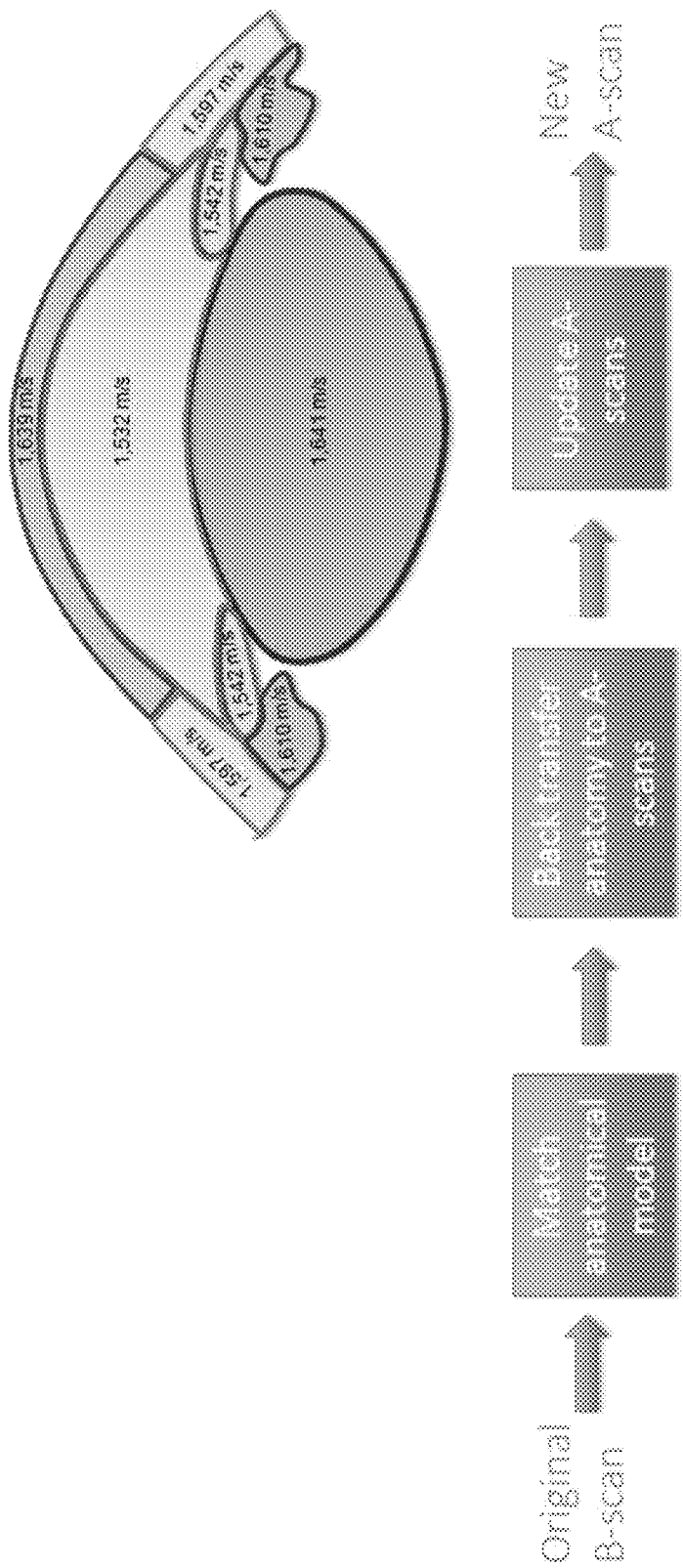
FIG. 17 illustrates steps for a second method for correcting for speed of sound.

FIG. 16 and FIG. 17 illustrate steps in correcting for speed of sound. As noted previously, an ultrasound scanner record time-of-arrival of reflected ultrasound pulses. A speed of sound of the medium is then used to convert these time of arrival measurements to distance measurements. Traditionally, a single representative speed of sound value is used. As instrument resolution and precision improves, using a single speed of sound leads to positional errors that can affect the efficacy of an artificial lens prescribed on the basis, in part, of an ultrasound scanner. When using a single speed of sound, the speed of sound of water at 37C (1,531 m/s) is used although speeds of sound from 1,531 m/s to 1,641 m/s may be used.

FIG. 16 demonstrates the need for correcting for speed of sound. The speed of sound varies between about 1,524 m/s in water at 37° C. to about 1,641 m/s in a cataractous lens. When applying uniform speed of sound to covert the time base of a plurality of A-scans to a distance base, significant errors can be introduced into, for example, highly-detailed artificial lens sizing measurements. Artificial lenses include ICLs (implantable contact lenses) and AIOLs (accommodating intraocular lenses). The accuracy of the B-scan can be further improved by applying known values of the speed of sound, as shown in FIG. 17, in the various regions of the eye.

Other means can be used to determine a speed of sound appropriate for a region of an eye. For example, U.S. Pat. No. 8,317,709 entitled "Alignment and Imaging of an Eye with an Ultrasonic Scanner" discloses a method for measuring the thickness of an eye component such as the cornea, aqueous fluid or the natural lens. FIG. 16 illustrates a method whereby a porcine cadaver eye is implanted with metallic pins of a known separation and scanned by a precision ultrasound scanner. The ultrasound scanner delivers accurate time-of-arrivals of ultrasound pulse reflecting between pins immersed in a target component which, used with the known pin spacing, can produce an accurate speed of sound.

To form a more accurate B-scan, the following steps are representative of a first procedure for adjusting a series of A-scans for the best possible speeds of sound known for each region of an eye of the anterior segment. These regions include the cornea, the aqueous fluid, the lens and several regions of scleral tissue (see FIG. 6).

The speed of sound varies in the different anterior segment regions of the eye such as the cornea, aqueous, natural lens and vitreous fluid. The speed of sound in these different regions have been measured by various researchers and are reasonably known. Therefore if the interfaces of these regions can be identified, the appropriate speeds of sounds for these regions can be used to convert times of arrivals to distances with more accuracy. The accepted speeds of sound for various eye components is shown in FIG. 17.

FIG. 17 illustrates how the anatomical model shown can be deformed to match a particular B-scan of an eye of interest using image or edge-based registration. This anatomical model can be used as a mask over a B-scan to identify and map each region with a different speed of sound. This, in turn, allows a computer algorithm to re-apply the appropriate speed of sound to each anatomical region of the A-scan.

Adjusting for Speed of Sound in Various Regions of the Eye

Method 1

1. select a scan type—for example, one of an arcuate scan, a linear scan and scans of various radii of curvature including inverse radii of curvature
2. select an average speed of sound for the eye for planning approximate scan times and for creating a rough image. Traditionally, a single representative speed of sound value is used. Usually the speed of sound of water at 37C (1,531 m/s) is used although speeds of sound from 1,531 m/s to 1,641 m/s may be used (1,641 m/s is the speed of sound in a cataractous lens).
3. generate a series of ultrasound pulses for each single scan type
4. receive the reflected ultrasound signals—an A-scan of analogue volts versus time
5. use an A/D converter to digitize each A-scan—an A-scan of digitized volts versus time
6. perform an envelope calculation of each A-scan (digitized volts versus time). The envelope is obtained by doing a Fourier transform of the A-scan, removing the negative frequency components and then doing an inverse Fourier transform to obtain the envelope. Alternately, the envelope can be obtained by using the Hilbert function.
7. from the envelope of the A-scans, determine the eye component interface time-of-arrivals The interfaces include the anterior and posterior cornea and lens. See FIGS. 11 and 19. The interface time-of-arrivals are the local maxima of the pulses identified.
8. from the eye component interface time of arrivals, determine the approximate interface positions using the selected average speed of sound.
9. identify eye component regions (cornea, aqueous, lens) see map
10. using speed of sound speed map of FIG. 6, apply speed of sound corrections to each A scan (which turns A-scans into volts vs distance)
11. apply grayscale algorithm—turns volts into grayscale brightness
12. plot grayscale brightness versus distance to form a sound speed adjusted B-scan Method 2

Figure 18:
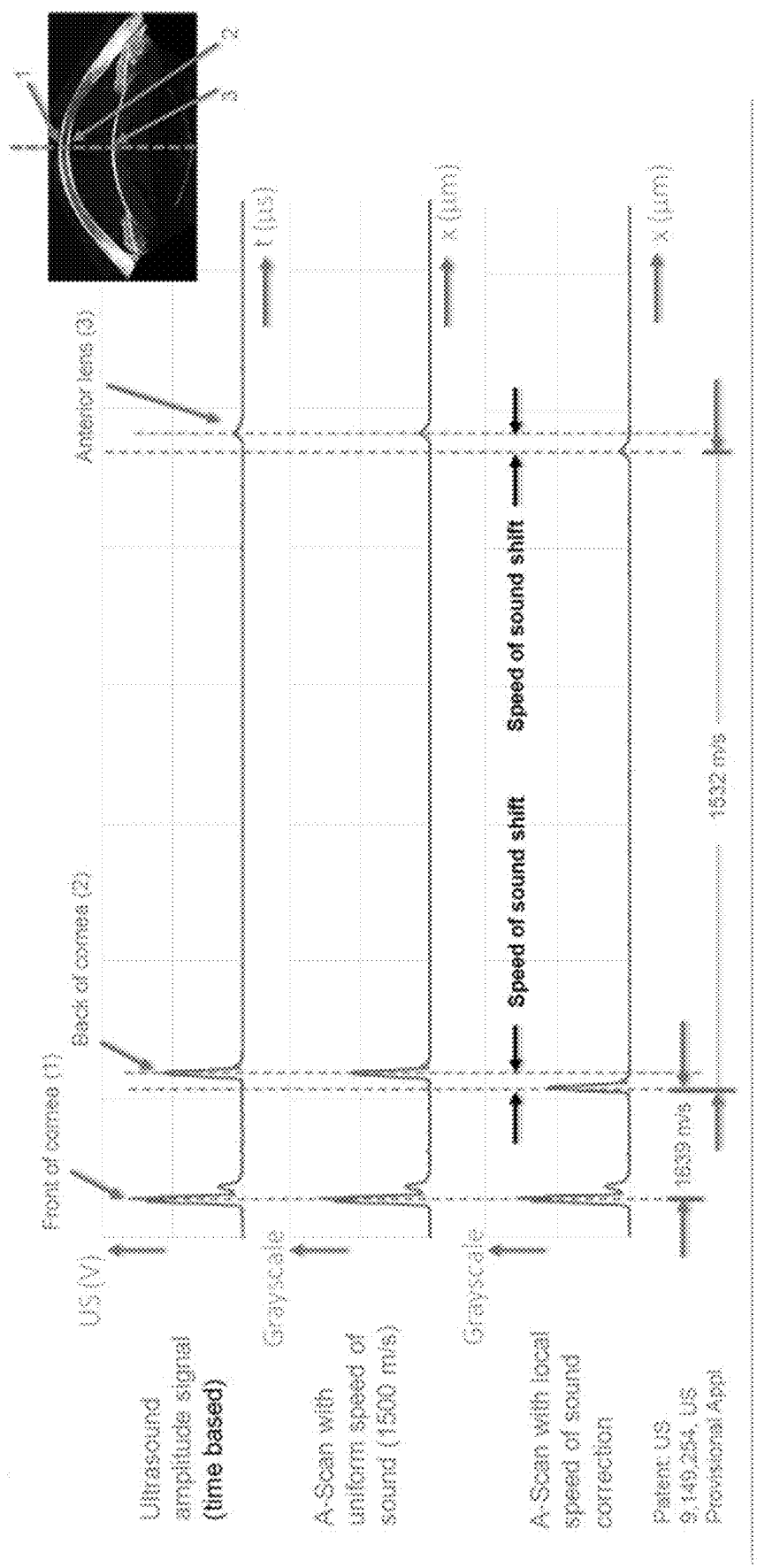
FIG. 18 illustrates the progression of steps for correcting a B-scan for speed of sound.
Figure 19:
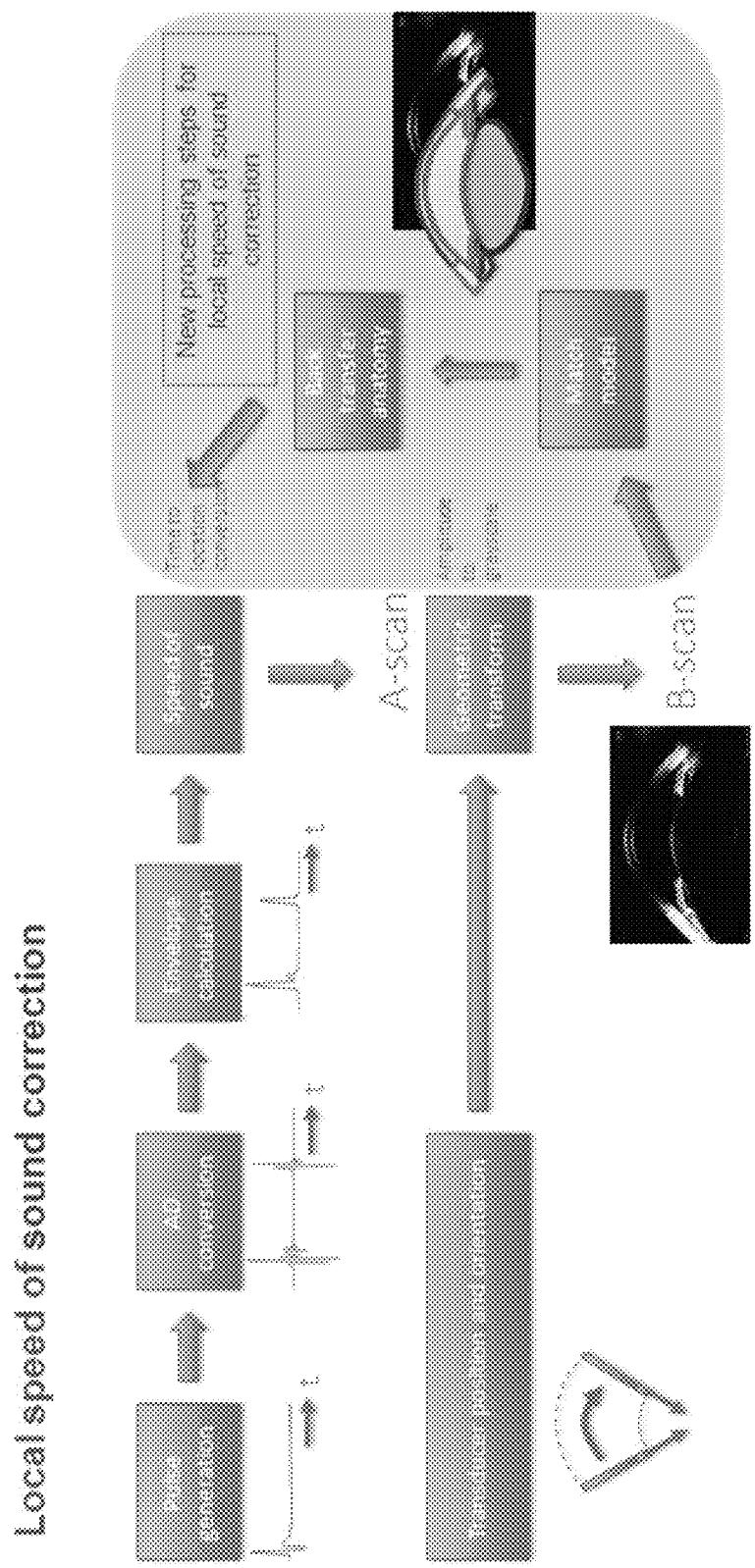
FIG. 19 illustrates the steps for a second method for correcting for speed of sound.

The following steps are representative of a second procedure for adjusting a B-scan to account for speeds of sound known for each region of an eye of the anterior segment. FIGS. 17, 18 and 19 illustrate this second method for correcting for speed of sound.

The principal steps are:

1. select a scan type—for example, one of an arcuate scan, a linear scan or scans of various radii of curvature including inverse radii of curvature
2. select an average speed of sound for the eye for creating a first detailed image. Traditionally, a single representative speed of sound value is used. Usually the speed of sound of water at 37C (1,531 m/s) is used although speeds of sound from 1,531 m/s to 1,641 m/s may be used (1,641 m/s is the speed of sound in a cataractous lens).
3. generate a series of ultrasound pulses for each single scan type
4. receive the reflected ultrasound signals—an A-scan of analogue volts versus time
5. use an A/D converter to digitize each A-scan—an A-scan of digitized volts versus time 6. perform an envelope calculation of each A-scan (digitized volts versus time). The envelope is obtained by doing a Fourier transform of the A-scan, removing the negative frequency components and then doing an inverse Fourier transform to obtain the envelope. Alternately, the envelope can be obtained by using the Hilbert function.
7. apply grayscale algorithm—turns volts into grayscale brightness. The algorithm may be a linear or non-linear conversion from volts to grayscale brightness
8. Apply a geometric transformation that combines the transducer location and orientation with the A-scans to form a B-scan image
9. refer to an anatomical model that identifies the regions with different speeds of sound. The model must be deformable to be able to match onto any eye (e.g., statistical shape model, deformable masks). See FIGS. 17 and 26.
10. digitally match the anatomical model onto the B-scan image using, for example, image or edge-based registration
11. Use the matched anatomical model to identify the ranges in each of the original A-scans corresponding to particular anatomical eye components
12. Apply the correct local speed of sound to the identified anatomical ranges in each A-scan to correct for local speed of sound changes
13. re-apply the geometric transformation using the updated A-scans with anatomically-corrected local speed of sounds to obtain a local speed-of-sound corrected new B-scan.

FIG. 18 illustrates the progression of steps for correcting an A-scan for speed of sound. This figure shows a corrected A-scan as described in Step 4 of the description of FIG. 13. The A-scan of FIG. 18 is that for the anterior segment of the eye (anterior cornea to anterior lens). The top trace shows amplitude in volts versus time in microseconds. The middle trace shows a rough conversion of the abscissa to distance in microns using a single approximate speed of sound. The ordinate has been transformed from volts to a grayscale unit. The bottom trace shows the abscissa shifted by applying a more accurate speed of sound to each region. These regions are the cornea (1,639 m/s), the aqueous (1,532 m/s) and the lens (1,641 m/s).

FIG. 19 illustrates the steps for a second method for correcting for speed of sound. An ultrasound pulse is generated by the transducer and its echo or reflected pulse is received by the transducer. The received analogue pulse is converted to digital format by an A/D converter. The digitized signal is then processed by applying an FFT and computing the envelope of the processed signal (volts versus time). The envelope is converted to volts versus distance by applying an average speed of sound (typically the speed of sound of water at about 38 degrees centigrade). The transducer position and orientation data is then used on each corrected A-scan to form an array of corrected A-scans in an x-y-z-beta co-ordinate system. The array of corrected A-scans is then used to form a preliminary B-scan based on a single average speed of sound.

The anatomical model shown in FIG. 17 is deformed to match the preliminary B-scan using image or edge-based registration. This anatomical model can be used as a mask over a B-scan to identify and map each region with a different speed of sound. This match model is then used to provide a final B-scan corrected for the best available speed of sound for each region.

Figure 20:
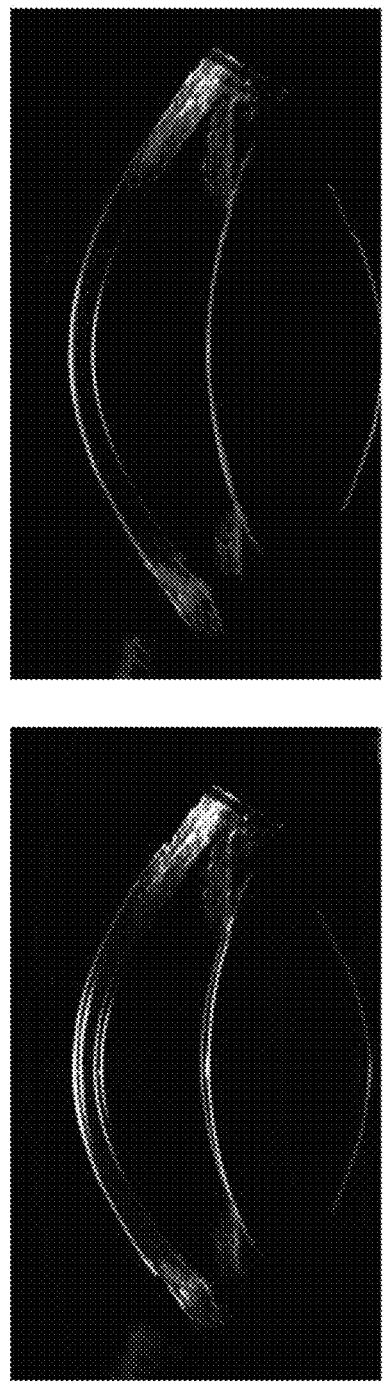
FIG. 20 illustrates image registration for removal of eye movement artifacts.

FIG. 20 illustrates image registration for removal of eye movement artifacts. During scanning, the patient's eye can move or the scanner can vibrate under the motion of the transducer. The patient's eye can move due to saccades, for example, which are quick, simultaneous rotations of both eyes in the same direction involving a succession of discontinuous individual rotations of the eye orbit in the eye socket. The movement of the transducer during a scan can be slowed to avoid instrument vibration but it is desirable to move the transducer probe as rapidly as possible to reduce scan time. If there is movement of the eye or movement of the scanner, image registration can reduce the effects of eye movements between sweeps. As described previously, the B-scan of FIG. 20 comprises several intermediate B-scans and, when combined to form a composite image may not align perfectly. The individual B-scans can be better aligned by overlaying one of the specular surfaces (such as the anterior cornea or anterior lens) to bring the separate images into much better alignment as shown in FIG. 20.

The image registration illustrated in FIG. 20 is described above in steps 1 and 2 of the principal steps for creating a stitched or composite image.

Figure 21:
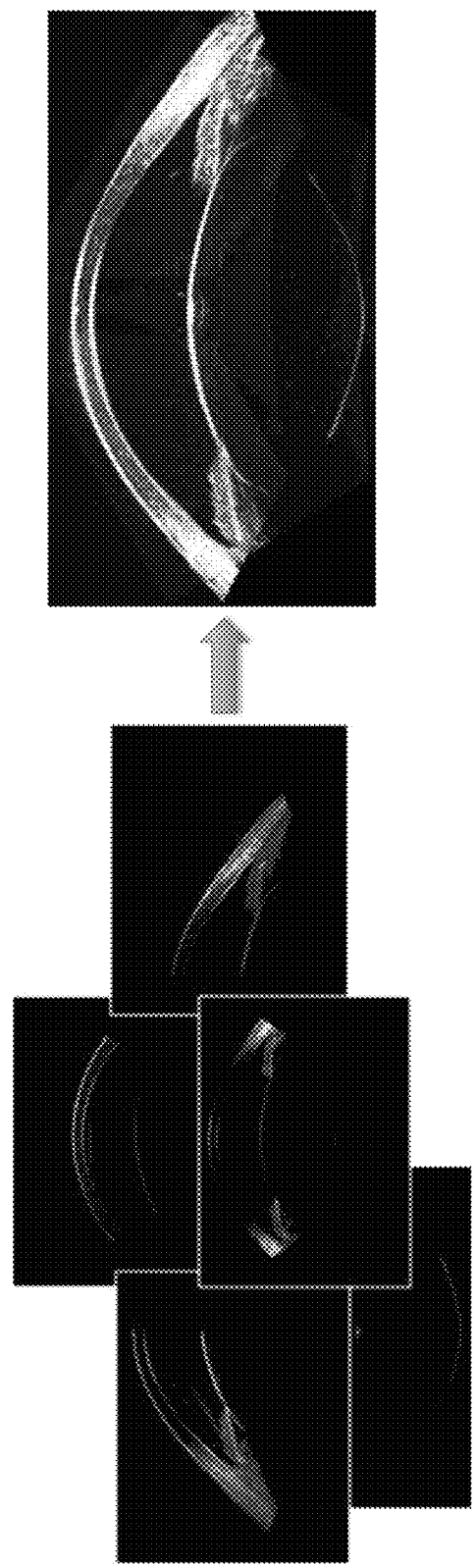
FIG. 21 illustrates image compositing.

FIG. 21 illustrates image compositing wherein image registration is used to combine multiple optimized image sweeps. The perpendicularity requirement for optimal ultrasound imaging means that different adjacent anatomical structures may be imaged optimally by different scan types or probe sweeps (probe trajectories). To create a complete picture of the anatomy of the eye, registering and merging images from different sweeps enables the display of anatomically correct combinations of these images. The initial registration from instrument position data is critical for rapid convergence of high precision registration. The image registration illustrated in FIG. 21 is described above in steps 3 to 6 of the principal steps for creating a stitched or composite image.

Sequence of Operations to Produce a B-Scan

Figure 22:
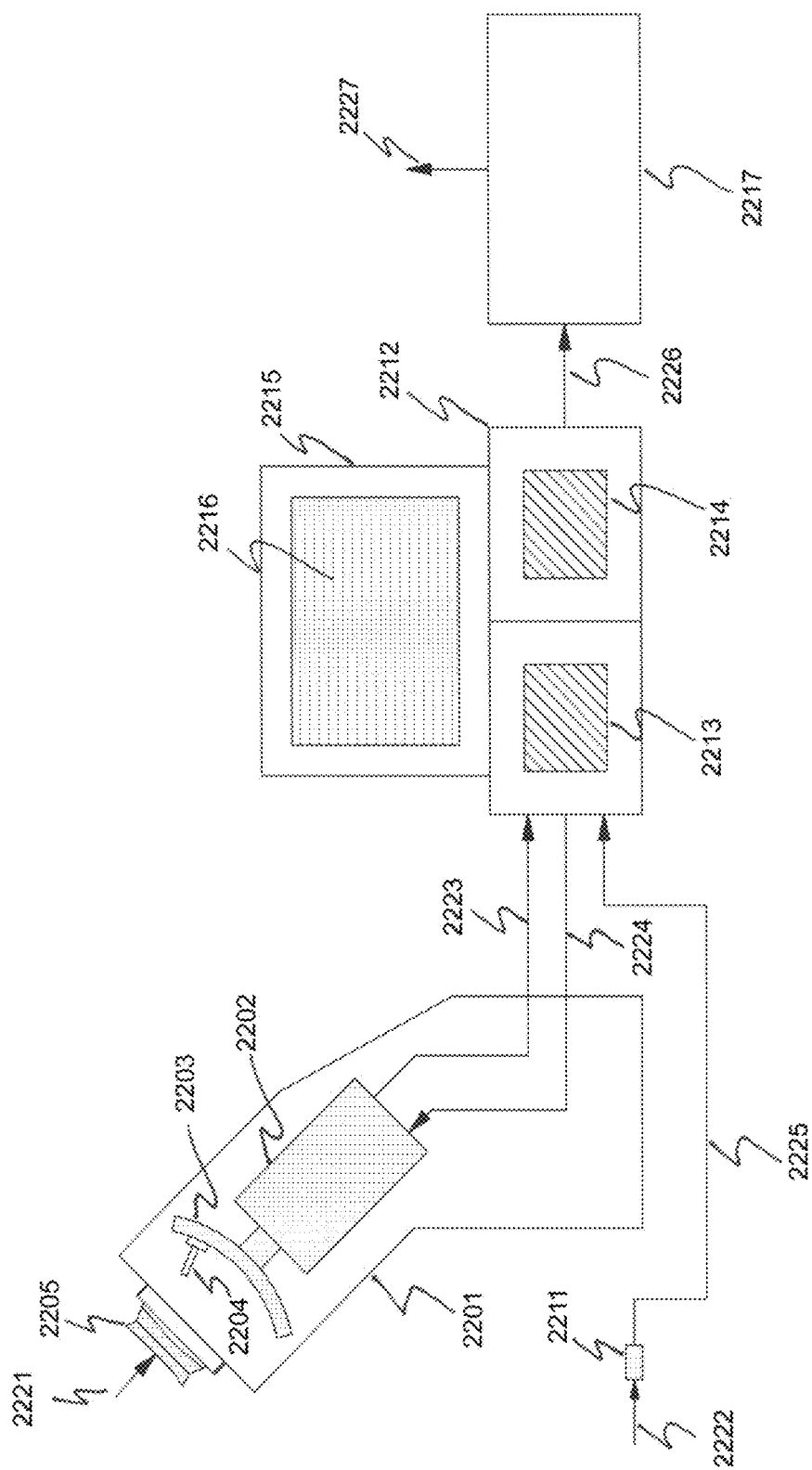
FIG. 22 is a schematic representation of the control functions of an arc scanning apparatus.
Figure 23:
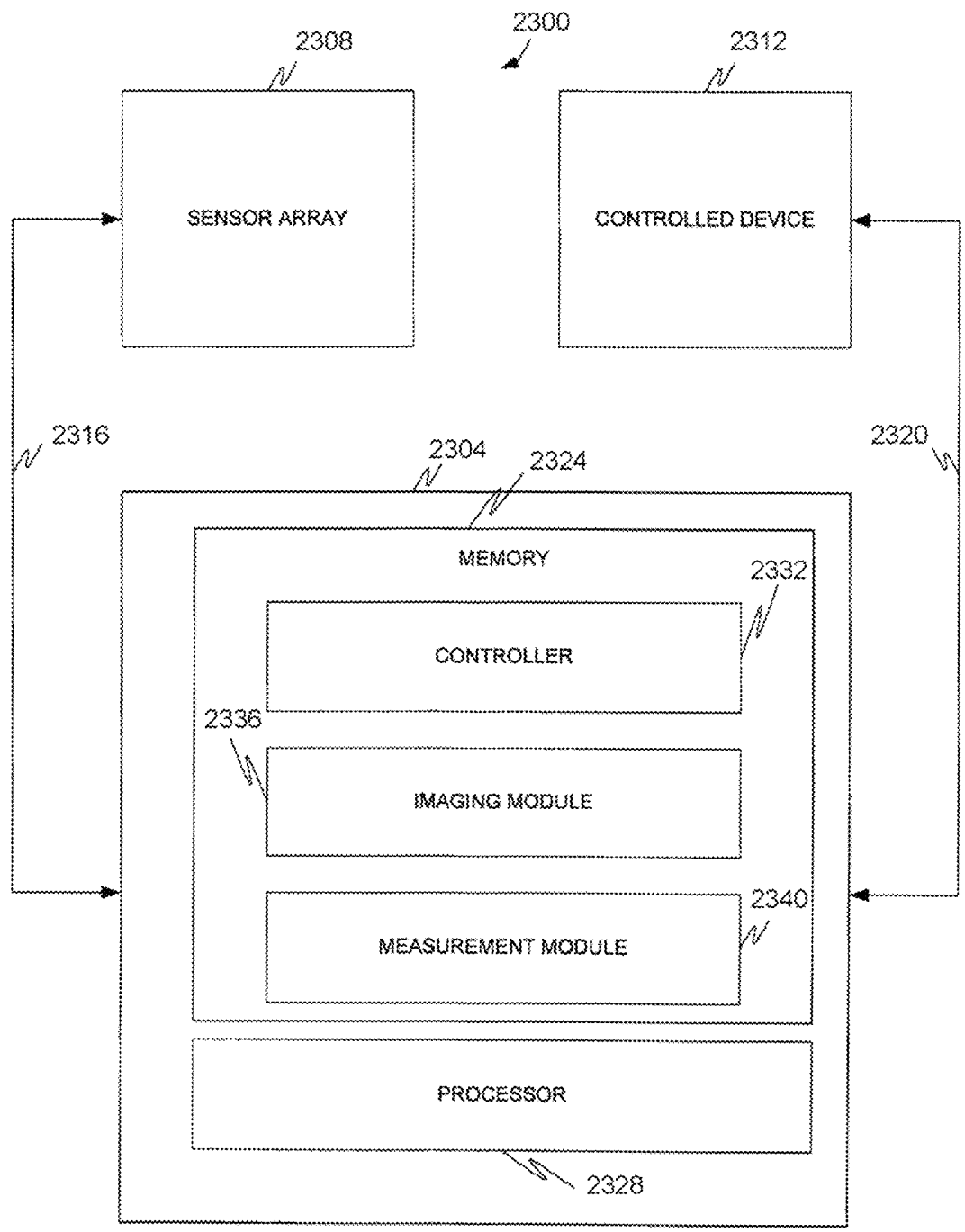
FIG. 23 depicts a control and signal processing system for any of the embodiments of the present disclosure discussed above.
Figure 24:
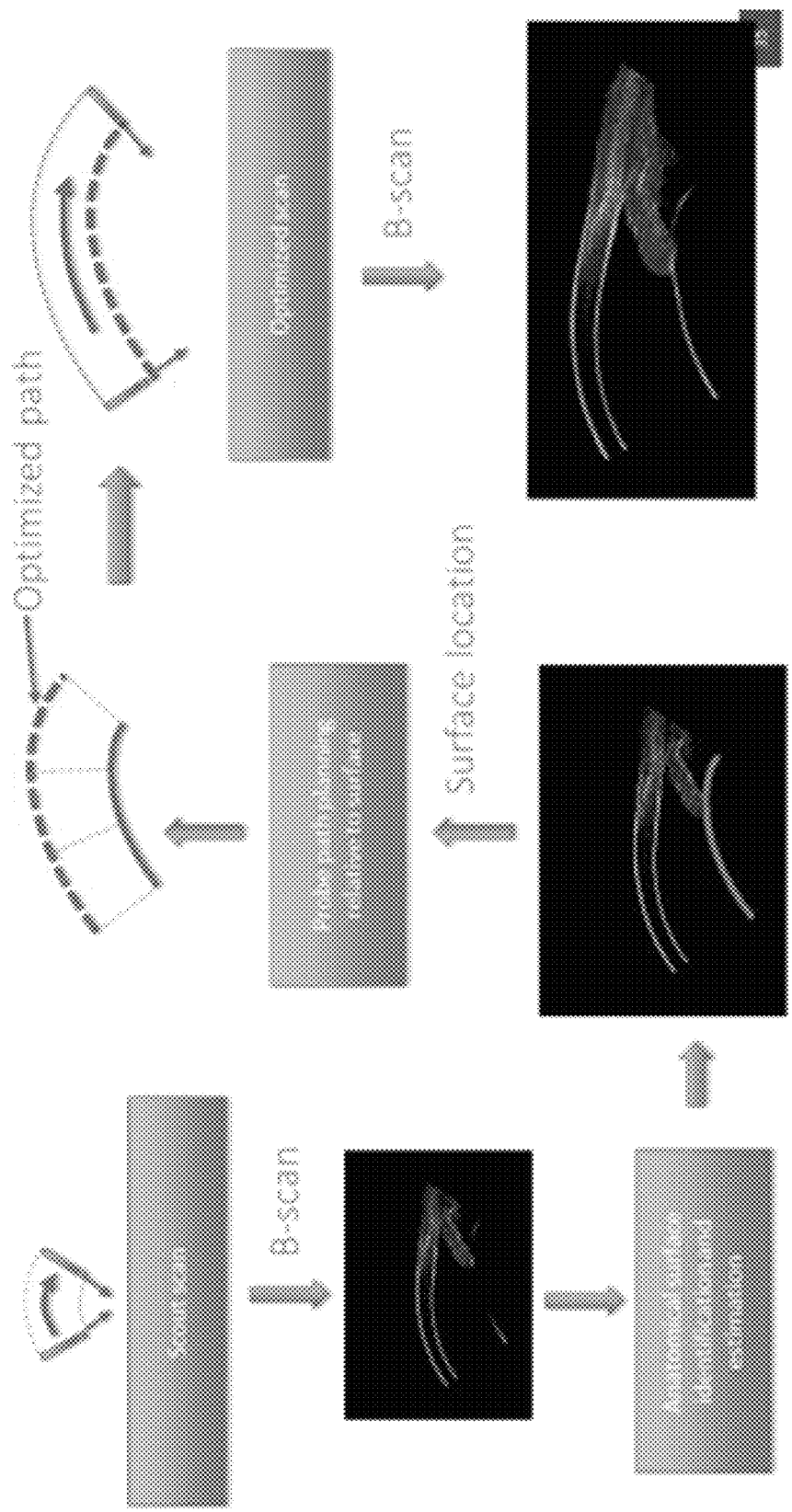
FIG. 24 illustrates an example of a method in which a scout image is used to determine the optimal trajectory of the transducer for generating a more optimal image.

FIGS. 22, 23 and 24 illustrate the principal steps to form a B-Scan. These are:
14. generate an ultrasound pulse with a transducer
15. receive the reflected pulse with the transducer and convert it to digital form (A/D conversion)
16. determine transducer position and orientation for all emitted/received pulses from the magnetic encoders on the arcuate and linear guide tracks and on the scan head positioner mechanism
17. calculate the envelope of each digitized reflected pulse
18. apply a single speed of sound of the medium to convert digitized envelope from a time base to a distance base
19. convert the amplitude of each digitized envelope to a grayscale value (low grayscale values are black shading to grey and then to white at high grayscale values)
20. assemble each digitized grayscale vs distance trace into a B-scan using the transducer position and orientation data The result of the above process is a B-scan image that has been formed by applying a single appropriate value for speed of sound in an eye. The accuracy of the B-scan can be further improved by applying known values of the speed of sound in various regions of the eye. These regions include the cornea, the aqueous fluid, the natural lens and the scleral tissue.

Control and Signal Processing

FIG. 22 is a schematic representation of the control functions of an arc scanning apparatus. The arc scanning apparatus is comprised of an arc scanning machine 2201 which includes an arc guide positioning mechanism 2202, an arc guide (or arcuate guide or arc track) 2203, an ultrasonic transducer 2204 and a disposable eyepiece 2205. The arc scanning apparatus may also include a more complex scan head in which an arcuate guide track is mounted on a linear guide track. This arrangement is shown, for example, in FIG. 7. The arc scanning machine 2201 is connected to a computer 2212 which includes a processor module 2213, a memory module 2214 and a video monitor 2215 with video screen 2216. The computer 2212 is connected to an operator input device such as a mouse 2211 and/or a keyboard (not shown). The computer 2212 is also connected to an output device such as, for example, a printer or internet connection 2217. The patient is seated at the machine 2201 with their eye engaged with disposable eyepiece 2205 such as described in FIG. 2. The patient's eye component to be imaged is represented by input 2221. The operator using mouse and/or keyboard 2211 and video screen 2216 inputs information 2222 into computer 2212 selecting the type of scan and scan configurations as well as the desired type of output image and analyses. The operator, using mouse and/or keyboard 2211, a video camera in scanning machine 2201 and video screen 2216, then centers a set of cross hairs displayed on video screen 2216 on the desired component of the patient's eye, also displayed on video screen 2216, setting one of the cross hairs as the prime meridian for scanning. Once this is accomplished, the operator instructs computer 2212 using either mouse and/or keyboard 2211 to proceed with the scanning sequence. Now the computer processor 2213 takes over the procedure and issues instructions via path 2224 to the positioning head 2202, the arcuate track 2203 and the transducer carriage 2205 and receives positional and imaging data via path 2223 which is stored in memory module 2214. The computer processor 2213 proceeds with a sequence of operations such as for example: (1) rough focus transducer 2204 on the selected eye component; (2) accurately center arcuate track 2204 with respect to the selected eye component; (3) accurately focus transducer 2204 on the selected feature of the selected eye component; (4) rotate the arcuate track through a substantial angle and repeat steps (1) through (3) on a second meridian; (5) rotate the arcuate track back to the prime meridian; (6) initiate a set of A-scans along each of the of selected scan meridians, storing this information in memory module 2214; (7) utilizing processor 2213, converting the A-scans for each meridian into a set of B-scans and then processing the B-scans to form an image associated with each meridian; (8) performing the selected analyses on the A-scans, B-scans and images associated with each or all of the meridians scanned; and (9) outputting 2227 the data in a preselected format to an output device such as printer 2217. The output can also be stored in memory module 2214 for later retrieval on video screen 2216, or for transmission to remote computers or other output devices via any number of well-known data transmission means.

FIG. 23 depicts a control and signal processing system for any of the embodiments of the present disclosure discussed above. The system 2300 includes a sensor array 2308 and a controlled device 2312 in signal communication via, duplexed channels 2318 and 2320, with a computer 2304.

The sensor array 2308 comprises linear or angular position sensors that, among other things, track the relative and/or absolute positions of the various movable components and the alignment of various stationary and moveable components, such as, but not limited to, the one or more position tracking sensors, the positioning arms 603 and 703 and probe carriage assembly 604, the fixation lights 621, 622, the optical video camera 623, the arcuate guide assembly 704, the ultrasound transducer probes 605, 705 and 805, the probe carriage 708, the linear guide track 720, the OCT probes 731, 831, the OCT reference arms 732, 832, the OCT recording apparatus 735, the probe carriage 804, the optical delay line 836, the collimators 838 and 839, the fixed mirror, the broad band light source 841, the spectrometer 842, the motors to move the position arms, motors to move the arcuate guide assembly, and motors to move the probe carriage. The sensor array may comprise any suitable type of positional sensors, including inductive non-contact position sensors, string potentiometers, linear variable differential transformers, potentiometers, capacitive transducers, eddy-current sensors, Hall effect sensors, proximity sensors (optical), grating sensors, optical encoders (rotary or linear), and photodioide arrays. Candidate sensor types are discussed in U.S. Pat. No. 8,758,252.

The controlled device 2312 is any device having an operation or feature controlled by the computer 2304. Controlled devices include the various movable or activatable components, such as, but not limited to, the one or more position tracking sensors, the positioning arms 603 and 703, the transducer carriage assembly 604, the fixation lights 621, 622, the optical video camera 623, the arcuate guide assembly 704, the ultrasound transducer probes 605, 705 and 805, the probe carriage 708, the linear guide track 720, the OCT probes 731, 831, the OCT reference arms 732, 832, the OCT recording apparatus 735, the probe carriage 804, the optical delay line 836, the collimators 838 and 839, the fixed mirror, the broad band light source 841, the spectrometer 842, the motors to move the position arms, motors to move the arcuate guide assembly, and motors to move the probe carriage.

The computer 2304 may comprise a software-controlled device that includes, in memory 2324, a number of modules executable by a processor 2328. The executable modules include a controller 2332 to receive and process positioning signals from the sensor array 2308 and generate and transmit appropriate commands to the monitored controlled device 2312, an imaging module 2336 to receive and process A- and B-scan images to produce two-, three-, or four-dimensional images of selected ocular components or features, and a measurement module 2340 to determine, as discussed above, the dimensions and/or volumes of selected ocular components and/or features. The imaging algorithm used by the imaging module 2336 is further discussed U.S. Pat. No. 8,496,588.

In one embodiment, the controller 2332 determines an adjustment to the position of the transducer and/or the OCT sample arm probe and the OCT reference arm based on receiving a control measurement input from the sensor array 2308. In another embodiment, the controller 2332 provides a control input to the drive mechanism of the probe carriage, the positioning arm, the arcuate guide assembly, and/or the linear guide track. In yet another embodiment, the controller 2332 provides a control input to comprise controlling the power, frequency, signal/noise ratio, pulse rate, gain schedule, saturation thresholds, and sensitivity of the optical and/or ultrasound transducers. In still another embodiment, the controller 2332 utilizes control algorithms comprising at least one of on/off control, proportional control, differential control, integral control, state estimation, adaptive control and stochastic signal processing. Controller 2332 may also monitor and determine if any faults or diagnostic flags have been identified in one or more elements, such as the optical and/or ultrasound transducers and/or carriage.

In yet another embodiment, the disclosed systems and methods may be partially implemented in software that can be stored on a storage medium to include a computer-readable medium, executed on programmed general-purpose computer with the cooperation of a controller and memory, a special purpose computer, a microprocessor, or the like. In these instances, the systems and methods of this disclosure can be implemented as program embedded on personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

In one embodiment, one or more computers are used to control, among other things, the combined UHFU and OCT imaging system, the scan head assembly, the OCT sample arm probe, OCT reference arm, and/or the ultrasound transducer and/or the position sensor(s). In one embodiment, the user interacts with the computer through any means known to those skilled in the art, to include a keyboard and/or display to include a touch-screen display. The term "computer-readable medium" as used herein refers to any tangible storage and/or transmission medium that participate in providing instructions to a processor for execution. Such a medium may take many forms, including but not limited to, non-volatile media, volatile media, and transmission media. Non-volatile media includes, for example, NVRAM, or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a CD-ROM, any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored.

Use of an Ultrasound Scout Image

As used herein, a scout image is an image taken in order to scope out the anatomy of interest in the eye in preparation for a more useable image showing the anatomy of interest in more detail or from a different, more useable angle. The scout image may be used or deleted as appropriate. A scout image or scout view is a preliminary image obtained prior to performing the important elements of a particular study and is used, for example, to image locations where more features of interest may be obtained. Many ultrasound technicians or doctors consider scout images to be merely a guide for improving subsequent image quality (contrast and brightness). In many instances however, scout images can show critical diagnostic information that is not displayed on the more detailed images taken after the scout image.

An ultrasound scout image can be made from any of the scan types described above but is more commonly generated by the simpler scan types such as a cornea scan, an anterior segment scan, a central posterior capsule scan or a left and right segment scan of the posterior capsule.

FIG. 24 illustrates an example of a method in which a scout image is used to prepare for generating a more optimal image. In this example, the image sought is an image of the right equatorial diameter of the lens by planning a probe trajectory that aims for a substantially perpendicular ultrasound beam path and optimal focal distance of the ultrasound beam to a now known surface.

As illustrated, starting in the upper left corner of FIG. 24, a simple anterior segment scan with a radius of curvature of about 7 to 11 mm, with the patient rotating his or her eye to their left, is made to generate a B-scan image of the right side of an eye showing the cornea, iris and the region of the eye around the iridocorneal angle and the scleral spur. From this image, the anatomical surfaces near the right equatorial diameter of the lens are identified. Then a more optimal transducer probe path is planned such as, for example, a tight radius of curvature of about 4 mm or a variable radius of curvature starting with a radius of curvature of about 10 mm and grading to a radius of curvature of about 4 mm. This new probe trajectory then generates an optimized B-scan of the right side of an eye as shown in the lower right corner of FIG. 24, which is the image sought.

A Method to Enhance Measurement of the Lens Capsule Diameter

Parts of the following was taken from "Methods to Estimate the Size and Shape of the Unaccommodated Crystalline Lens in Vivo" which describes methods capable of estimating the size and shape of the human eye lens without resorting to phakometry or magnetic resonance imaging (MRI). Previously published biometry and phakometry data of 66 emmetropic eyes of 66 subjects (age range 18 to 63 years) were used to define multiple linear regressions for the radii of curvature and thickness of the lens, from which the lens refractive index could be derived. MRI biometry was also available for a subset of 30 subjects, from which regressions could be determined for the vertex radii of curvature, conic constants, equatorial diameter, volume, and surface area. All regressions were compared with the phakometry and MRI data; the radii of curvature regressions were also compared with a method proposed by Bennett and Royston et al.

One way to improve estimates of, for example, lens equatorial diameter is to accurately measure anterior and posterior radii of curvature of the lens, especially by measuring points behind the iris, and then, using one of the relations established by MRI images, extrapolate the surfaces obtained by imaging.

To perform accurate ray tracing inside the human eye, it is important to know the in vivo size and shape of the lens. Although the equivalent power of the lens can be easily calculated, obtaining a reliable estimate of its dimensions is more difficult because lens biometry, except for lens thickness, requires dedicated equipment that is available only as experimental devices.

This work uses previously published biometry and phakometry data 24 of 66 eyes of 66 emmetropes (32 male, 34 female; 62 Caucasian, 4 non-Caucasian) with a mean age of 42.4 years, over the range of 19 to 69 years of age.

Subjects' eyes were not dilated nor cyclopleged before testing. This might have caused some degree of accommodation in the younger subjects, resulting in slightly more myopic refraction, increased lens thickness, and decreased anterior chamber depth.

The Bennett-Royston equation for lens power in diopters is:

$$P_L = -1000n(S_{CV}+K)/(1000n-(ACD+c_1T)(S_{CV}+K)) + 1000n/(-c_2T+V) \quad (1)$$

where:
n=refractive index of aqueous and vitreous humors=1.336
$S_{cv}$=spherical refraction due to ICL (diopters)
K=corneal power (diopters)
ACD=anterior chamber depth (mm)
T=lens thickness (mm)
$C_1$=0.571
$C_2$=−0.378
V=vitreous depth (mm)=L−ACD−T
L=axial length (mm)

As can be seen, the axial length, L, must be known to use this formula.

Corneal power, K, may be calculated from "On Calculation of Power from Curvature of the Cornea" as:

$$F=(1/r_1)(n_1-n_0)+(1/r_2)(n_2-n_1)-d(1/r_1)(n_1-n_2)(1/r_2)(n_2-n_1) \quad (2)$$

where:
$r_1$=anterior cornea radius of curvature (m)
$r_2$=posterior cornea radius of curvature (m)
$n_0$=index of refraction of air=1.000
$n_1$=index of refraction of the cornea=1.376
$n_2$=index of refraction of the aqueous=1.336
d=reduced thickness of the cornea=D/n
n=refractive index
D=thickness of the cornea (m)

Figure 25:
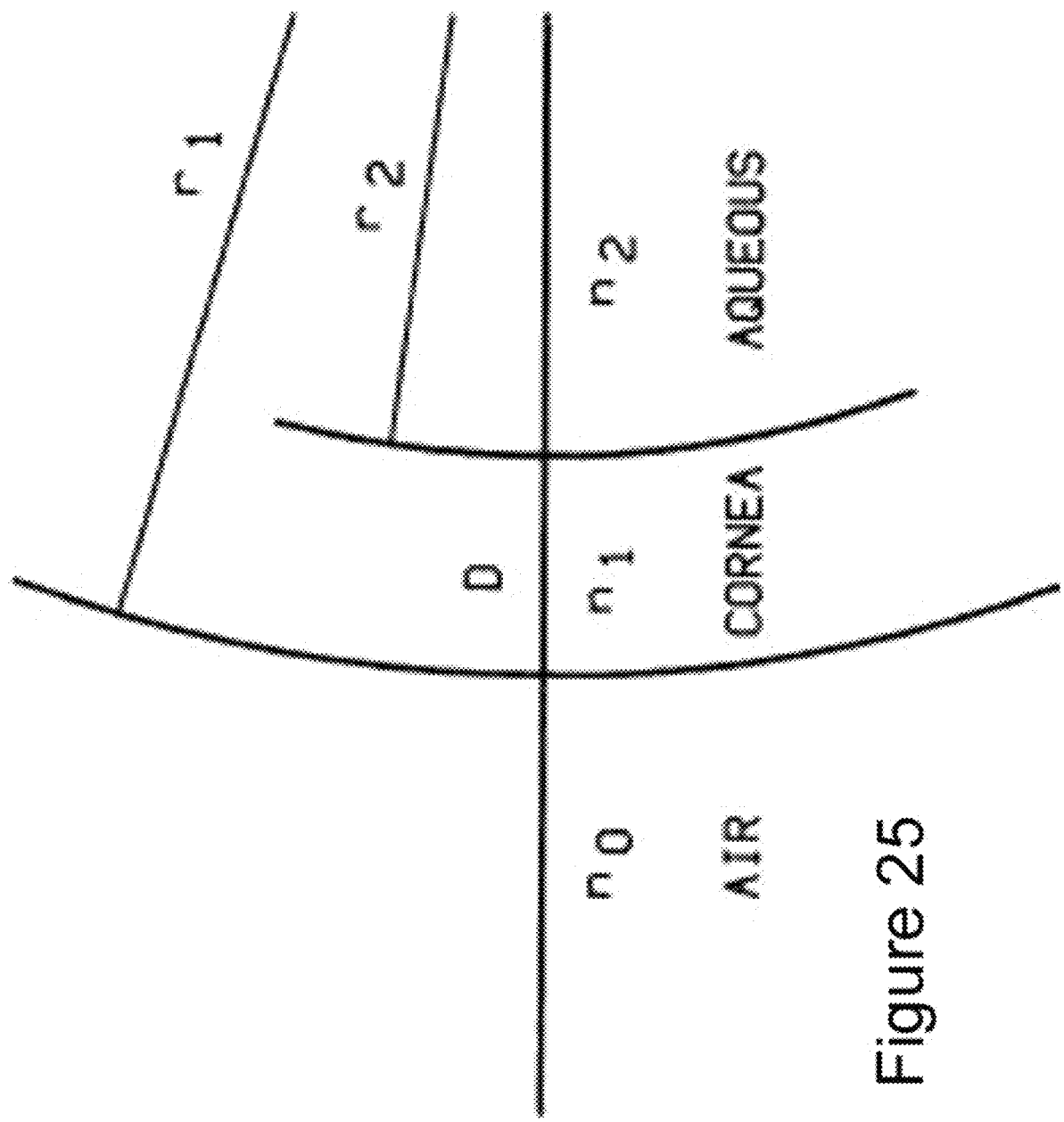
FIG. 25 shows the indices of refraction for regions of the anterior segment of an eye.

The regions of the anterior segment of an eye for refractive indices $n_0$, $n_1$ and $n_2$ are shown in FIG. 25.

Once we have $P_L$ from Equation 1, the lens anterior and posterior radii of curvature can be estimated from:

$$r_{1a}(S)=1000(n_L-n)/(Q\,P_L) \quad (3)$$

$$T_{1p}(S)=1000C_2(n_L-n)/(c_1Q\,P_L) \quad (4)$$

where:
$n_L$=1.431
Q=0.405

These radii of curvature can be compared with those measured by the Insight 100.

Conversely, if $r_{1a}(S)$ and $r_{1p}(S)$ are measured, then equation (2) can be solved for $P_L$ and n.

As an alternative to the Bennett-Royston method, r1a[S] and r1p[S] can be estimated using a multiple linear regression of lens thickness, T, and estimated lens power, $P_L$, as follows:

$$r_{1a}(S)=26.02-2.7T-0.2P_L \quad (5)$$

$$r_{1p}(S)=-16.75+1.696T+0.126P_L \quad (6)$$

It can be seen that, by measuring r1a(S) and $r_{1p}(S)$ and T with the Insight 100, $P_L$ can then be estimated.

Using a smaller subgroup of MRI subjects, the following relations were developed for $r_{1a}$ and $r_{1p}$ and the conic constants $k_{1a}$ and $k_{1p}$.

$$r_{1a}(A)=18.49-2.7T-0.62P_L \quad (7)$$

$$r_{1p}(A)=-11.98+0.27P_L \quad (8)$$

$$k_{1a}=3.99-2.61T+0.58P_L \quad (9)$$

$$k_{1p}=0.52+0.58T-0.1P_L \quad (10)$$

The conic constants $k_{1a}$ and $k_{1p}$ are used in the equation:

$$y=x^2/(r+\sqrt{(r^2-kx^2)}) \quad (11)$$

| | |
|---|---|
| k > 0 | oblate elliptical |
| k = 0 | spherical |
| 0 > k > −1 | prolate elliptical |
| k = −1 | parabolic |
| K < −1 | hyperbolic; and lens and mirror surfaces |

Figure 26:
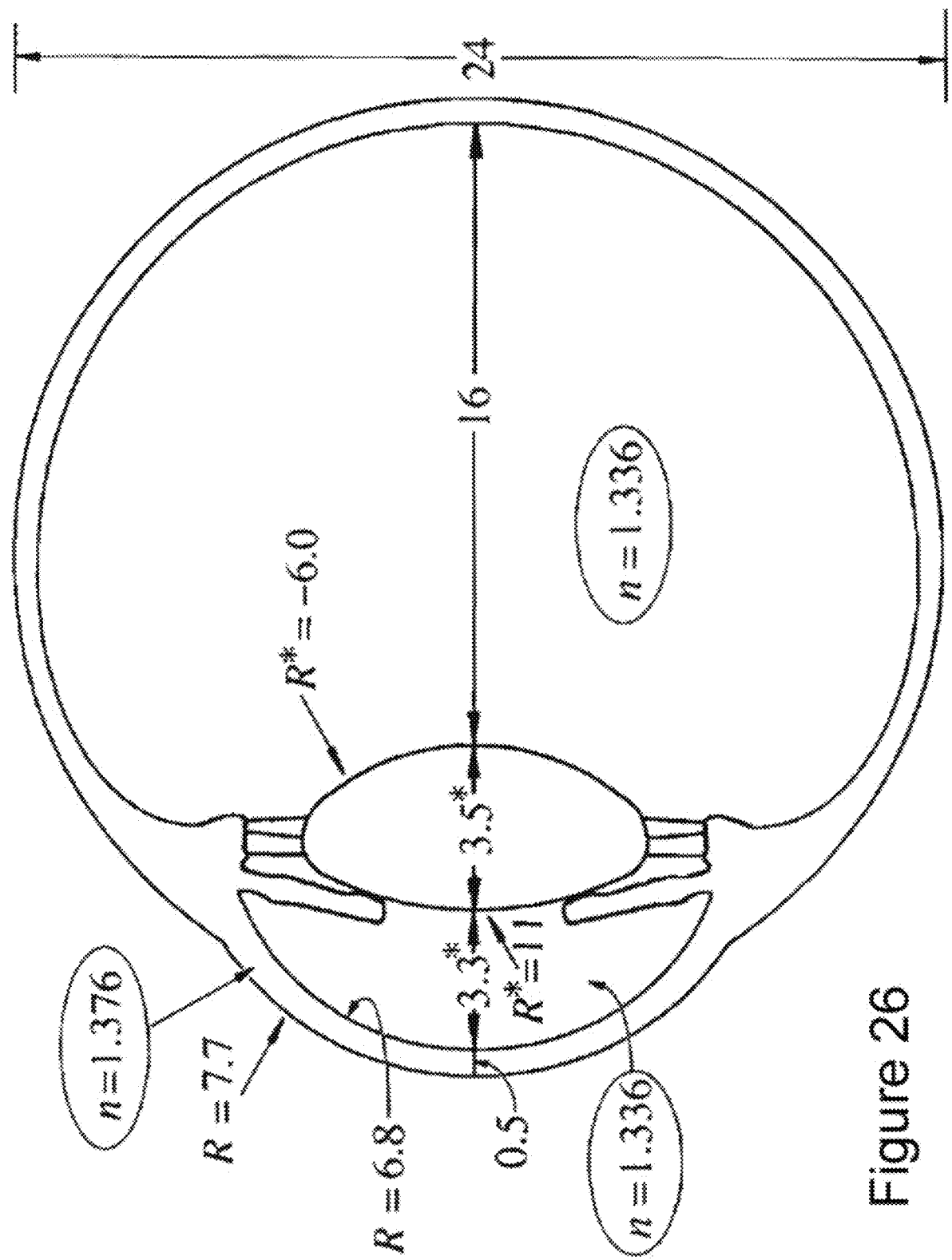
FIG. 26 shows typical dimensions for the human eye.

FIG. 26 shows typical dimensions for the human eye in millimeters:
$r_{ca}$=7.7
$r_{cp}$=6.8
$D_c$=0.5
$n_c$=1.376
ACD=3.3
$n_{aqueous}$=1.336
$r_{1a}$=11.0
$r_{1p}$=6.0
T=3.5
$n_1$=1.431
$L_{axial}$=23.3

| | | |
|---|---|---|
| Lens anterior | Kla = 8.85344 | oblate elliptical |
| Lens posterior | Klp = 0.13648 | oblate elliptical |

Figure 27:
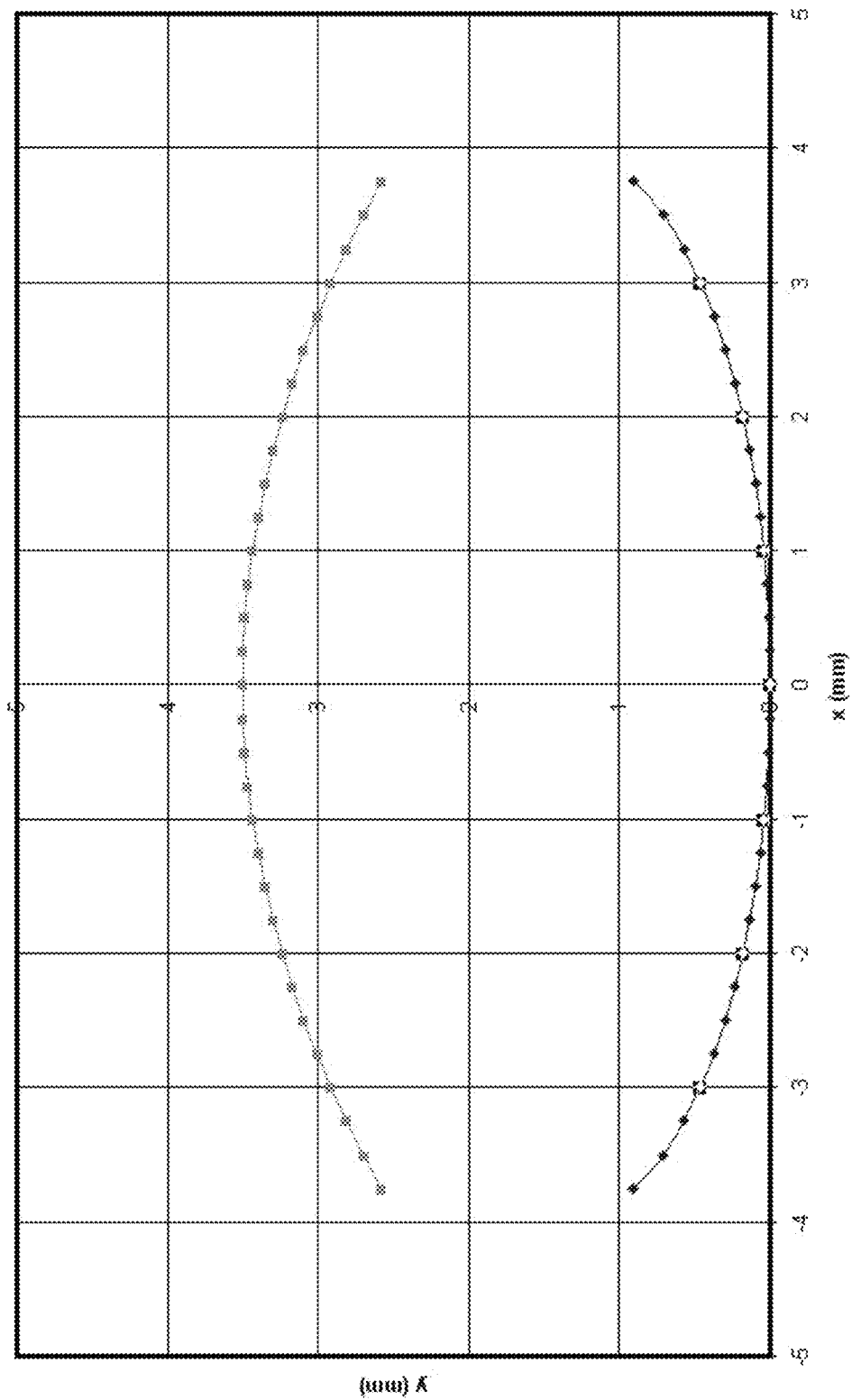
FIG. 27 shows typical dimensions for the natural lens.

FIG. 27 shows typical dimensions for the natural lens.

Once, ACD, T and $P_L$ are known, an estimate of lens equatorial diameter can be made:

$$Dc=8.34+0.39ACD+0.32T-0.08P_L \quad (12)$$

Also, the lens volume and surface diameter can be estimated.

$$Vol=-271.71+48.67T+10.27L \quad (13)$$

$$Surf=-106.26+17.72T+8.76L \quad (14)$$

Measuring the Lens Radii of Curvature r1a[S] and rlp[S] using the Insight 100

The anterior and posterior surfaces of the lens are characterized by the maximum amplitude grayscale points along each surface. Any 3 of these points, preferably near the optical axis will define the radius of curvature. From the Insight 100 data, several sets of 3 points can be used to find an average radius of curvature for the anterior and posterior surfaces of the lens. Alternately, all the points on the surface may be used to find a least squares fit to circle for which its radius of curvature is obtained.

Similarly, using Insight 100 data, several sets of 3 points can be used to find an average radius of curvature for the anterior and posterior surfaces of the cornea.

The Lens Maker's Equation is:

$$1/f=(n-1)(1/R_1-1/R_2+(n-1)t/(n\,R_1R_2)) \quad (15)$$

This formula is also the formula for a thick lens.
1/f=the optical power of the lens
n=the refractive index of the lens material
R1=the radius of curvature of the lens surface closet to the light source. A positive radius of curvature indicates the surface's center of curvature is further along in the direction of the ray travel.
R2=the radius of curvature of the lens surface furthest from the light source. A negative radius of curvature means that the rays reaching the surface have already passed the center of curvature. If R1>0 and R2<0, then the lens is a convex lens such as the natural lens. If R1>0 and R2>0, the lens is a concave lens such as the cornea.

Age Related Variables

Approximate lens thickness (on the visual axis) as a function of age:

$$T=4.845+0.019 \text{ Age}-0.444 ACD \quad (16)$$

Other variables, some related to age:

| Parameter | Age Dependent Relaxed Eye |
|---|---|
| Anterior Corneal Radius (mm) | 7.8 |
| Posterior Corneal Radius (mm) | 6.5 |
| Corneal Thickness (mm) | 0.55 |
| Refractive Index, air | 1 |
| Refractive Index, cornea | 1.376 |
| Refractive Index, aqueous | 1.336 |
| Refractive Index, vitreous | 1.336 |
| Equivalent Refractive Index, lens | 1.441 − 0.00039 Age |
| Anterior Chamber Depth (mm) | 3.87 − 0.01 Age |
| Anterior lens Radius (mm) | 12.9 − 0.057 Age |
| Posterior Lens Radius (mm) | −6.2 + 0.012 Age |
| Lens Thickness (mm) | 2.93 + 0.024 Age |
| $r_{ca}$ = 7.7 (mm) | |
| $r_{cp}$ = 6.8 (mm) | |
| $D_c$ = 0.5 (mm) | |
| $n_c$ = 1.376 | |
| ACD = 3.3 (mm) | |
| $n_{aqueous}$ = 1.336 | |
| $r_{la}$ = 11.0 (mm) | |
| $r_{lp}$ = 6.0 (mm) | |
| T = 3.5 (mm) | |
| $n_l$ = 1.431 | |
| $L_{axial}$ = 23.3 (mm) | |

The way in which these relations may be used is as follows:

$ from a B-scan of the anterior segment, measure the radii of curvature of the anterior and posterior cornea
$ from a B-scan of the anterior segment, measure the radii of curvature of the anterior and posterior of the lens
$ using the conic constants calculated from equation (6) above, construct an ellipse
$ digitally match the ellipse onto the B-scan or composite B-scan of the lens
$ determine the equatorial diameter of the ellipse
$ use the diameter of the ellipse so determined to estimate or constrain or the true diameter of the lens A number of variations and modifications of the inventions can be used. As will be appreciated, it would be possible to provide for some features of the inventions without providing others.

The present disclosure, in various embodiments, includes components, methods, processes, systems and/or apparatus substantially as depicted and described herein, including various embodiments, sub-combinations, and subsets thereof. Those of skill in the art will understand how to make and use the present disclosure after understanding the present disclosure. The present disclosure, in various embodiments, includes providing devices and processes in the absence of items not depicted and/or described herein or in various embodiments hereof, including in the absence of such items as may have been used in previous devices or processes, for example for improving performance, achieving ease and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover though the description of the disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A process for planning a trajectory for an ultrasound probe, comprising:
   providing a preliminary ultrasound scout image of an anatomy of interest based on a first path of travel of the ultrasound probe;
   identifying a location of the anatomy of interest based on the preliminary ultrasound scout image;
   determining a different second path of travel of the ultrasound probe to image the anatomy of interest based on the identified location;
   generating, by passing the ultrasound probe along the second path of travel, first and second grayscale images of the anatomy of interest, wherein each of the first and second grayscale image is associated with a respective ultrasound probe position and orientation;
   overlaying first and second grayscale images based on the respective ultrasound probe positions and orientations and moving the first and second grayscale images relative to each other;
   determining an alignment parameter at each relative position between the first and second grayscale images until the alignment parameter is at an extremum at one relative position; and
   combining the first and second grayscale images on a pixel-by-pixel at the one relative position with the extremum to form a composite grayscale image.

2. The process of claim 1, wherein when aligned pixels have a value above a predetermined threshold in both the first and second grayscale images, intensities of the aligned pixels from aligned pixels are averaged together as a pixel value in the composite grayscale image and wherein the determining of the different second path of travel of the ultrasound probe to image the anatomy of interest based on the identified location comprises selecting, based on the identified location of the anatomy of interest and as the second path of travel, a trajectory of the ultrasound probe that optimally images the anatomy of interest by maximizing perpendicularity of an ultrasound beam relative to a selected surface of the anatomy of interest while maintaining the anatomy of interest at a focal length of the probe during one or more imaging sweeps of the ultrasound probe.

3. The process of claim 2, wherein when aligned pixels have a value above the predetermined threshold in only one of the first and second grayscale images, the intensity of the aligned pixels above the predetermined threshold is used as the pixel value in the composite grayscale image.

4. The process of claim 1, wherein determining the alignment parameter is a sum of squared residuals from each pixel and the extremum is a minimum value of the sum.

5. The process of claim 2, wherein the predetermined threshold is an intensity value from a grayscale color scheme.

6. The process of claim 1, further comprising translating and rotating the first and second grayscale images relative to each other to move the first and second grayscale images relative to each other.

7. The process of claim 1, wherein the ultrasound probe is operably connected to an arcuate track and linear track and further comprising:
   scanning an eye of a patient with the ultrasound probe in a third path of travel after the eye of the patient rotates to one side,
   generating a B-Scan from signals received by the ultrasound probe moving in the third path of travel, wherein at least one anatomical surface of the eye of the patient is identified;
   scanning the at least one anatomical surface of the eye of the patient with the ultrasound probe in a fourth path of travel after the eye of the patient rotates to the one side, wherein the fourth path of travel is distinct from the third path of travel; and
   generating another B-Scan from the signals received by the ultrasound probe moving in the fourth path of travel.

8. The process of claim 7, further comprising:
   combining the B-Scan associated with a fourth path of travel with at least one other B-Scan to produce a composite image of a lens of the eye;
   determining an equatorial diameter of the lens of the eye from radii of curvature of an anterior and a posterior of a cornea of the lens and from radii of curvature of an anterior and a posterior of the lens; and
   adjusting A-Scans that form the B-Scan associated with the third path of travel by dividing signal-versus-time data by a first sound speed in a first non-specular region and by a distinct, second sound speed in a second non-specular region.

9. An arc spanning apparatus comprising:
   an arc guide;
   an ultrasound transducer positioned on the arc guide;
   an arc guide positioning mechanism to controllably position the ultrasound transducer along the arc guide;
   an eyepiece to receive an eye of a patient for scanning by the ultrasound transducer;
   a computer; and
   an operator input device to input information into the computer, wherein the computer causes the arc scanning apparatus to:
   provide a preliminary ultrasound scout image of an anatomy of interest based on a first path of travel of the ultrasound transducer;
   identify a location of the anatomy of interest based on the preliminary ultrasound scout image;
   determining a different second path of travel of the ultrasound transducer to image the anatomy of interest based on the identified location;
   generate, by passing the ultrasound transducer along the second path of travel, first and second grayscale images of the anatomy of interest, wherein each of the first and second grayscale image is associated with a respective ultrasound probe position and orientation;
   overlay first and second grayscale images based on the respective ultrasound probe positions and orientations and moving the first and second grayscale images relative to each other;
   determine an alignment parameter at each relative position between the first and second grayscale images until the alignment parameter is at an extremum at one relative position; and
   combine the first and second grayscale images on a pixel-by-pixel basis at the one relative position with the extremum to form a compositive grayscale image.

10. The apparatus of claim 9, wherein when aligned pixels have a value above a predetermined threshold in both the first and second grayscale images, intensities of the aligned pixels from aligned pixels are averaged together as a pixel value in the compositive grayscale image.

11. The apparatus of claim 10, wherein when aligned pixels have a value above the predetermined threshold in only one of the first and second grayscale images, the intensity of the aligned pixels above the predetermined threshold is used as the pixel value in the composite grayscale image.

12. The apparatus of claim 9, wherein determining the alignment parameter is a sum of squared residuals from each pixel and the extremum is a minimum value of the sum.

13. The apparatus of claim 10, wherein the predetermined threshold is an intensity value from a grayscale color scheme.

14. The apparatus of claim 9, further comprising translating and rotating the first and second grayscale images relative to each other to move the first and second grayscale images relative to each other.

15. The apparatus of claim 9, wherein the determining of the different second path of travel of the ultrasound transducer to image the anatomy of interest based on the identified location comprises selecting, based on the identified location of the anatomy of interest and as the second path of travel, a trajectory of the ultrasound transducer that optimally images the anatomy of interest by maximizing perpendicularity of an ultrasound beam relative to a selected surface of the anatomy of interest while maintaining the anatomy of interest at a focal length of the ultrasound transducer during one or more imaging sweeps of the ultrasound transducer and wherein the arc guide comprises an arcuate track and linear track and wherein the computer causes the arc scanning apparatus to:
   scan an eye of a patient with the ultrasound transducer in a third path of travel after the eye of the patient rotates to one side;
   generate a B-Scan from signals received by the ultrasound transducer moving in the third path of travel, wherein at least one anatomical surface of the eye of the patient is identified;
   scan the at least one anatomical surface of the eye of the patient with the ultrasound transducer in a fourth path of travel after the eye of the patient rotates to the one side, wherein the fourth path of travel is distinct from the third path of travel; and
   generate another B-Scan from the signals received by the ultrasound transducer moving in the fourth path of travel.

16. The apparatus of claim 15, wherein the computer causes the arc scanning apparatus to:
  combine the B-Scan associated with the fourth path of travel with at least one other B-Scan to produce a composite image of a lens of the eye;
  determine an equatorial diameter of the lens of the eye from radii of curvature of an anterior and a posterior of a cornea of the lens and from radii of curvature of an anterior and a posterior of the lens; and
  adjust A-Scans that form the B-Scan associated with a third path of travel by dividing signal-versus-time data by a first sound speed in a first non-specular region and by a distinct, second sound speed in a second non-specular region.

17. A process for planning a trajectory for an ultrasound probe, comprising:
  providing a preliminary ultrasound scout image of an eye of a patient based on a first path of travel of the ultrasound probe;
  identifying a location of at least one anatomical surface of the eye based on the preliminary ultrasound scout image;
  determining a different second path of travel of the ultrasound probe to image the at least one anatomical surface of the eye based on the identified location;
  generating a B-Scan from signals received by the ultrasound probe moving in the second path of travel, wherein the at least one anatomical surface of the eye of the patient is identified;
  scanning the at least one anatomical surface of the eye of the patient with the ultrasound probe in a second path of travel after the eye of the patient rotates to one side, wherein the second path of travel is distinct from the first path of travel;
  generating another B-Scan from the signals received by the ultrasound probe moving in the second path of travel;
  combining the B-Scan associated with the second path of travel with at least one other B-Scan to produce a composite image of a lens of the eye; and
  determining an equatorial diameter of the lens of the eye from radii of curvature of an anterior and a posterior of a cornea of the lens and from radii of curvature of an anterior and a posterior of the lens.

18. The process of claim 17, wherein the determining of the different second path of travel of the ultrasound probe to image the at least one anatomical surface based on the identified location comprises selecting, based on the identified location of the at least one anatomical surface and as the second path of travel, a trajectory of the ultrasound probe that optimally images the at least one anatomical surface by maximizing perpendicularity of an ultrasound beam relative to a selected surface of the at least one anatomical surface while maintaining the at least one anatomical surface at a focal length of the probe during one or more imaging sweeps of the ultrasound probe and further comprising adjusting A-Scans that form the B-Scan associated with the first path of travel by dividing signal-versus-time data by a first sound speed in a first non-specular region and by a distinct, second sound speed in a second non-specular region.

19. The process of claim 17, further comprising:
  generating, by passing the ultrasound probe along a third path of travel, first and second grayscale images of an anatomy of interest, wherein each of the first and second grayscale images is associated with a respective ultrasound probe position and orientation;
  overlaying first and second grayscale images based on the respective ultrasound probe positions and orientations and moving the first and second grayscale images relative to each other;
  determining an alignment parameter at each relative position between the first and second grayscale images until the alignment parameter is at an extremum at one relative position; and
  combining the first and second grayscale images on a pixel-by-pixel basis at the one relative position with the extremum to form a composite grayscale image.

20. The process of claim 19, wherein when aligned pixels have a value above a predetermined threshold in both the first and second grayscale images, intensities of the aligned pixels from aligned pixels are averaged together as a pixel value in the composite image, wherein when aligned pixels have a value above the predetermined threshold in only one of the first and second grayscale images, the intensity of the aligned pixels above the predetermined threshold is used as the pixel value in the composite image, wherein determining the alignment parameter is a sum of squared residuals from each pixel and the extremum is a minimum value of the sum, wherein the predetermined threshold is an intensity value from a grayscale color scheme, and further comprising translating and rotating the first and second grayscale images relative to each other to move the first and second grayscale images relative to each other.

* * * * *

UNITED STATES PATENT AND TRADEMARK OFFICE
CERTIFICATE OF CORRECTION

PATENT NO. : 12,329,572 B2
APPLICATION NO. : 18/537379
DATED : June 17, 2025
INVENTOR(S) : Johan E. Giphart et al.

It is certified that error appears in the above-identified patent and that said Letters Patent is hereby corrected as shown below:

In the Claims

At Column 34, Line 49, after "pixel-be-pixel" insert --basis-- therein.

At Column 35, Line 45, please delete "spanning" and insert --scanning-- therein.

At Column 35, Line 61, please delete "determining" and insert --determine-- therein.

At Column 36, Line 13, please delete "compositive" and insert --composite-- therein.

At Column 36, Line 18, please delete "compositive" and insert --composite-- therein.

Signed and Sealed this
Twenty-eighth Day of October, 2025

John A. Squires
*Director of the United States Patent and Trademark Office*